(12) United States Patent
Leijssen et al.

(10) Patent No.: US 11,517,283 B2
(45) Date of Patent: Dec. 6, 2022

(54) MAGNETIC INDUCTIVE SENSING DEVICE AND METHOD

(71) Applicant: KONINKLIJKE PHILIPS N. V., Eindhoven (NL)

(72) Inventors: Jacobus Josephus Leijssen, Waalre (NL); Gerardus Johannes Nicolaas Doodeman, Veldhoven (NL); Rick Bezemer, Amsterdam (NL); Mark Peter Paul Kleijnen, Eindhoven (NL); Wouter Herman Peeters, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 785 days.

(21) Appl. No.: 16/475,411

(22) PCT Filed: Jan. 2, 2018

(86) PCT No.: PCT/EP2018/050055
§ 371 (c)(1),
(2) Date: Jul. 2, 2019

(87) PCT Pub. No.: WO2018/127488
PCT Pub. Date: Jul. 12, 2018

(65) Prior Publication Data
US 2019/0343417 A1 Nov. 14, 2019

(30) Foreign Application Priority Data
Jan. 9, 2017 (EP) ..................................... 17150641

(51) Int. Cl.
*A61B 7/00* (2006.01)
*A61B 5/08* (2006.01)
(Continued)

(52) U.S. Cl.
CPC ............ *A61B 7/003* (2013.01); *A61B 5/0816* (2013.01); *A61B 5/242* (2021.01); *A61B 5/243* (2021.01);
(Continued)

(58) Field of Classification Search
CPC .... A61B 2560/0462; A61B 2562/0223; A61B 2562/166; A61B 2562/182;
(Continued)

(56) References Cited

U.S. PATENT DOCUMENTS 4,714,887 A 12/1987 Meissner et al.
5,289,509 A 2/1994 Moeller
(Continued)

FOREIGN PATENT DOCUMENTS

WO 2006111877 A1 10/2006

OTHER PUBLICATIONS

International Search Report and Written Opinion, International Application No. PCT/EP2018/050055, dated Apr. 18, 2018.

*Primary Examiner* — Mark D Remaly

(57) ABSTRACT

The invention provides a magnetic inductive sensing device (30) comprising a loop antenna (10) for inductively coupling with electromagnetic (EM) signals emitted from a medium in response to stimulation of the medium with electromagnetic excitation signals. The device includes an electromagnetic shield (36) element which is arranged such as to intercept electromagnetic signals travelling to or from the antenna. The shield element is formed of conductive material such as to block electrical field components of incident signals but further incorporates a non-conductive gap in the material so as to prevent the formation of eddy currents. A loop of the antenna is broken by an opening, the opening being bridged by a capacitor, and the device comprises a signal processing means which is electrically coupled to the
(Continued)

antenna via only a single point of the antenna, located to one side of the opening.

15 Claims, 8 Drawing Sheets

(51) Int. Cl.
| | |
|---|---|
| *A61B 5/00* | (2006.01) |
| *H01Q 1/52* | (2006.01) |
| *H01Q 7/06* | (2006.01) |
| *A61B 7/02* | (2006.01) |
| *A61B 5/243* | (2021.01) |
| *A61B 5/242* | (2021.01) |
| *A61B 5/05* | (2021.01) |
| *G01R 29/08* | (2006.01) |
| *H04R 3/00* | (2006.01) |

(52) U.S. Cl.
CPC .......... *A61B 5/7203* (2013.01); *A61B 5/7225* (2013.01); *A61B 7/02* (2013.01); *H01Q 1/526* (2013.01); *H01Q 7/06* (2013.01); *A61B 5/05* (2013.01); *A61B 2560/0462* (2013.01); *A61B 2562/0223* (2013.01); *A61B 2562/166* (2013.01); *A61B 2562/182* (2013.01); *A61B 2562/222* (2013.01); *G01R 29/0878* (2013.01); *H04R 3/00* (2013.01)

(58) Field of Classification Search
CPC ... A61B 2562/222; A61B 5/05; A61B 5/0816; A61B 5/242; A61B 5/243; A61B 5/7203; A61B 5/7225; A61B 7/00; A61B 7/003; A61B 7/02; G01R 29/0878; H01Q 1/526; H01Q 7/06; H04R 3/00
See application file for complete search history.

(56) References Cited

U.S. PATENT DOCUMENTS

| | | |
|---|---|---|
| 5,355,275 A | 10/1994 | Goodier et al. |
| 8,639,312 B2 | 1/2014 | Clark et al. |
| 2014/0197832 A1 | 7/2014 | Driesel et al. |
| 2015/0374292 A1 | 12/2015 | Wyeth et al. |
| 2015/0379387 A1 | 12/2015 | Richley |

MAGNETIC INDUCTIVE SENSING DEVICE AND METHOD

This application is the U.S. National Phase application under 35 U.S.C. §371 of International Application No. PCT/EP2018/050055, filed on 2 Jan. 2018, which claims the benefit of European Application Ser. No. 17150641.3, filed 9 Jan. 2017. These applications are hereby incorporated by reference herein.

FIELD OF THE INVENTION

This invention relates to a magnetic inductive sensing device, and in particular a sensing device for inductively coupling with a body for sensing electromagnetic signals.

BACKGROUND OF THE INVENTION

Inductive sensing can be used as a means of non-invasive investigation of properties of a medium or body.

In one advantageous area of application, inductive sensing can be used as a means of non-invasively investigating physiological characteristics, in particular heart and lung dynamics. Inductive sensing is based on magnetic induction and has several advantages over conductive and capacitive sensing.

An advantage compared to conductive sensing, such as bio-impedance measurements, is that adhesive electrodes are not required; sensing may be performed without contact.

An advantage compared with capacitive sensing is that inductive sensing is based on magnetic fields rather than electric fields and as a result is more sensitive to changes at greater penetration depth inside the body, as opposed to those just occurring at skin level. This is because magnetic fields penetrate deeper into a body than electrical fields, and thus magnetic fields can be used to measure changes in properties deeper inside the body, whereas electrical fields are predominantly useful only for measuring changes in properties on the surface of the skin (e.g. permittivity of the skin).

Coil-based inductive sensors function by inductively coupling with electromagnetic signals (i.e. electromagnetic waves or oscillations), wherein propagation of the signals through the coil leads to a change in the current through the coil, which can be measured and used to sense properties of the propagated signal (including e.g. frequency spectrum, amplitude and phase pattern).

An electromagnetic excitation signal can be propagated into a body to be investigated. The excitation electromagnetic signal causes magnetic induction in the body, i.e. the generation of eddy currents in the tissue of the body due to the application of an external magnetic field. These eddy currents then in turn generate electromagnetic signals propagated out of the body which can be sensed by the coil.

Movements of tissue in the body can manifest in changes in volume of the tissue. These changes then cause amplitude and/or phase modulations of the electromagnetic signal which is emitted out of the body in response to the electromagnetic stimulation. By monitoring these changes, movement and size change of elements within the body can be detected and tracked.

For inductive sensing, only the magnetic field components of electromagnetic signals carry information pertaining to elements of a body or medium located beneath the surface. The electric field components originate solely from the surface of any body (arising due to electrostatic induction). The electric field components however can readily dominate the electromotive forces induced in the receiver antenna, obscuring magnetic field contributions, and thus reducing sensitivity of the system to the desired objects of investigation.

Hence the parasitic effects arising from the electrical field render it difficult to measure changes in magnetic properties of the medium or body, and hence seriously impede sensitivity of the inductive sensing system. Signal to noise ratio as a consequence is reduced.

A magnetic inductive sensing device offering improved signal to noise ratio of magnetic field components of electromagnetic signals is sought.

SUMMARY OF THE INVENTION

The invention is defined by the claims.

It is known that electromagnetic shielding can be used to block or attenuate electromagnetic fields. In electromagnetic shielding, fields are blocked by a barrier or shield made of conductive or magnetic material. Such a shield is called a Faraday shield.

Shielding a coil or antenna with a Faraday shield blocks propagation to or from the antenna of both electric and magnetic fields. Simply shielding the antenna in this way therefore impedes all functionality of the resulting sensing system.

The inventors of the present invention have accordingly devised a new shielding approach which enables improved sensitivity to magnetic field components while successfully shielding electric field components, and hence removing much ambient noise from the resultant sensed signal.

According to an aspect of the invention, there is provided an inductive sensing device for sensing electromagnetic signals emitted from a medium in response to propagation into the medium of electromagnetic excitation signals, comprising:

a loop antenna for inductively coupling with said electromagnetic signals emitted from the medium; and a blocking shield arranged to intercept electromagnetic signals propagating to or from the antenna, the shield comprising an electrically conductive body for blocking electrical components of incident signals, and wherein the body delimits at least one non-conductive gap for inhibiting induction of eddy currents within the body, wherein a loop of the antenna is broken by an opening, the opening being bridged by a capacitor, and wherein the device comprises a signal processing means, the means being electrically coupled to the antenna via only a single point of the antenna, located to one side of the opening.

The invention is based on adaptation of an electromagnetic shield to include one or more non-conductive breaks or gaps designed to prevent induction within the shield of eddy currents which generate a secondary magnetic field which cancels out the primary magnetic field generated by the coil or antenna. This configuration will be termed a 'slotted Faraday shield'.

When electromagnetic fields propagate to or from the antenna, the magnetic field components falling incident at any conductive body (including a shield) induce through magnetic induction (Faraday's law of induction) eddy currents within the body. In a shield, it is this which provides the magnetic field shielding effect since the eddy currents in turn induce a magnetic field of reverse directionality to that which was originally incident (Lenz' Law), thereby opposing or cancelling the original propagated magnetic field oscillations. Thus the magnetic field components are effectively blocked.

By including in the shield con-conductive gaps, the eddy currents cannot form, and hence the opposing field components which cancel out the propagating magnetic field oscillations are not generated. The magnetic field components of electromagnetic signals can hence travel through the shield.

By contrast, shielding of the electric field components, which operates via a different physical principle, continues to occur. Electric field shielding occurs through redistribution of electric charges within the shield's body upon incidence of electric field components of electromagnetic signals. Incidence of fields on one side of the shield re-distributes the charges in such a way that that they cancel the field components' effects on the alternate side.

Thus the shielding approach of the present invention efficiently blocks propagation of electric field components while permitting passage of magnetic field components. The parasitic effects of the electric fields are therefore suppressed, and signal to noise ratio of a resulting measurement signal derived from signals received at the antenna is increased.

Furthermore, a capacitor effectively divides a loop of the antenna into two parts (two wings), extending to either side of the capacitor. A signal processing means is electrically coupled to only one side of the antenna loop (to only one wing). The other side of the antenna loop is only connected to the signal processing means via the bridging capacitor. The consequence of this is that the antenna is only loosely coupled to the signal processing means, with the beneficial effect that the signal processing means does not heavily load the antenna loop. This improves the sensitivity of the signal-processing means system to incident electromagnetic signals.

The blocking shield is arranged in a propagation path of the antenna for intercepting electromagnetic signals propagating to or from the antenna. By propagation path may be meant for instance a spatial path through which electromagnetic emissions or signals naturally travel after emission from the antenna or when being received at the antenna.

By 'electromagnetic signals' is generally meant electromagnetic waves or oscillations, or electromagnetic radiation or emissions for instance. The term 'electromagnetic' denotes the general class of emission (signal), and does not for instance exclude purely electric field or purely magnetic field oscillations or waves.

By electromagnetic excitation signals is simply meant electromagnetic signals as described above emitted for the purpose of stimulating eddy currents in the medium in order to sense characteristics of the medium, as described above.

By 'electrically conductive body' may be meant a body (portion) of the shield comprising electrically conductive material.

By 'gap' may be meant broadly any interruption in the (continuous) conductivity of the body, for instance an interruption in the conductive material of the body. This interruption is to avoid a continuous conduction path through the body through which an eddy current might form.

The at least one gap may thus be positioned toward a periphery of the shield, since eddy currents are circuital, with the current typically circulating around a central point.

The at least one gap may be formed by a sub-region of the body formed of a less conductive material than surrounding material, for instance a sub-region of insulating material.

The at least one gap may comprise an opening through the conductive body. By opening is meant a space or break in the material of the conductive body, e.g. an air gap.

In accordance with one or more examples, the shield may comprise a laminar element, where this may be a flat, planar element or curved or contoured element.

The shield may in examples comprise a sheet element, where this may be a flat sheet element or a curved or contoured sheet element. The sheet element may be a plate element.

The shield may comprise a sheet element or plate element, arranged facing one planar side of the loop antenna, i.e. facing one planar side of the loop antenna.

The shield may in examples be a planar element.

In accordance with one or more sets of embodiments of the invention, the device may be a physiological inductive sensing device for sensing one or more physiological characteristics of a body of a subject.

As noted above, physiological inductive sensing is one particularly advantageous area of application for inductive sensing. It can be used as a means of non-invasively investigating many different physiological characteristics, including for instance heart and lung dynamics. The device may hence be a physiological, diagnostic or medical sensing device.

According to this set of embodiments, the system is for sensing electromagnetic signals received from a body of a subject in response to electromagnetic excitation signals applied to the body of the subject.

In such embodiments, the device may comprise a signal processing means coupled to the antenna for processing received electromagnetic signals to derive physiological information, such as indications of one or more physiological characteristics or parameters.

Alternatively, the device may be adapted for coupling to an external signal processing means in order to process signals received at the antenna, for instance to derive physiological information, characteristics or parameters.

The system may be a physiological parameter sensing system.

The system may be a vital sign sensing system. Vital signs may include for instance heart rate, pulse rate, breathing capacity and breathing rate.

Although physiological sensing is one area of application, the invention is not limited to such applications. The concept of the invention is applicable more generally to sensing electromagnetic signals received from any medium or body.

In accordance with any embodiment, the device may comprise a signal processing means for processing signals received at the antenna from the medium. The signal processing means may further be for deriving information or measurement indications pertaining to the medium.

The signal processing means may according to particular examples comprise signal processing circuitry or a microprocessor, or a microcontroller.

The signal processing means may be adapted to analyze or determine impedance of the antenna.

In accordance with other examples, the sensing device may not comprise a signal processing means, but may be adapted to be coupleable to an external or auxiliary signal processing means for processing signals received at the antenna.

In particular examples, the sensing device may further comprise a secondary shielding element adapted to block electromagnetic signals, the shielding element arranged to shield one or both of the capacitor bridging the loop antenna and the connection point between the antenna and the signal processing means.

This further shielding element makes the environment of these electronic components more defined and stable, since the electric field over the capacitor and/or the connection point is shielded.

The shielding element may in advantageous examples be a shielding enclosure arranged to enclose one or both of one or both of the capacitor bridging the loop antenna and the connection point between the antenna and the signal processing means.

By 'enclose' is simply meant surround, such as to shield the capacitor and the connection point from (substantially) all angles. Enclose does not necessarily require that the shielding element provides a fully seal around the capacitor and connection point.

In accordance with any embodiment, the shield may be arranged facing the antenna loop, and with the at least one gap aligned such as to extend across a circumference of the loop of the antenna.

By this may be meant that the gap as projected onto the antenna extends across a circumference of the loop of the antenna.

The function of the gap is to inhibit the development of eddy currents within the shield body conductive material in response to propagation through the body of magnetic flux (of electromagnetic signals travelling to or from the antenna). Fluxes falling incident on the shield will tend to induce eddy currents which circulate the incident irradiated area. Where these fluxes originate from the center of the antenna, the eddy currents induced in the shield will thus tend to map onto the periphery of the antenna loop (i.e. the loop circumference).

Hence, by locating the gap in a position such that it is aligned traversing or perpendicularly intersecting a projection of the antenna loop periphery on the shield, fluxes originating from a center of the antenna will be inhibited from generating eddy currents, since the natural circulatory path through which these currents form is interrupted by the gap. These signals will therefore not be blocked by the shield.

Likewise, fluxes of electromagnetic signals (originating from the medium) that are likely to reach and be successfully registered at the antenna will also tend to irradiate a region of the shield which maps onto the center of the antenna loop. These also therefore tend to generate eddy currents which map onto a periphery (circumference) of the loop of the antenna. Hence, a gap located in a position such that it is aligned traversing or perpendicularly intersecting the antenna loop periphery will inhibit generation of eddy currents caused by such electromagnetic signals. Accordingly, these signals will not be blocked by the shield.

In accordance with one or more embodiments, the shield may comprise a grounded plate element, and wherein the loop antenna is electrically coupled to the plate element in order to ground the loop. The plate element may be arranged on one planar side the antenna, i.e. facing one planar side of the antenna.

In accordance with this set of embodiments, the shield and antenna may be coupled together as an electrical system, with the shield grounding the antenna. The shield and antenna may be electrically coupled via an outer conductor of a coaxial cable, wherein an inner conductor of the co-axial cable is coupled to the antenna for connecting the antenna to a signal processing means.

The antenna may be positioned in planar alignment with the shield, with the antenna and the shield separated by a small separation clearance. The shield may be arranged facing the antenna with the gap aligned such as to extend across a circumference of the loop of the antenna.

The plate element may be a planar element.

To optimize impedance matching between the shield and the antenna, the location of the ground connection between the antenna and the shield may be adjusted. The voltage-current relationship changes as this connection point is moved around the circumference of the antenna loop. The position can hence be changed to optimize the impedance matching.

Optionally the loop antenna may be coupled to the shield via a capacitor. The capacitor provides an additional or alternative means for optimizing impedance matching between the antenna and the shield.

In accordance with any embodiment, the gap in the shield may extend inwardly from an edge of the conductive body. Optionally, the gap may extend from said edge to at least a central point of the conductive body. The gap may extend radially inward from an edge of the conductive body.

In accordance with these embodiments, the gap constitutes a slit or slot cutting in from an edge of the shield and effectively splits at least a portion of the shield into two.

A gap which extends from an edge at least to a central point (i.e. which extends radially from an edge to a central point) naturally tends to intersect (interrupt) any (circulatory) eddy current which attempts to form in the plate. In particular, any eddy current which, if formed, would circulate around a point proximal to the center point will be interrupted by such a slit and impeded from forming.

It is noted that by 'central point' is meant a point substantially at or toward the center or middle of the shield body, for instance at or proximal to a centroid of the shield body.

In accordance with any embodiment, the gap may comprise an opening through the conductive body. By opening is meant a space or break in (the material of) the conductive body, e.g. an air gap.

In accordance with any embodiment, the gap may be a slit or a slot in the conductive body. By slit or slot is generally meant a longitudinally dimensioned gap.

In accordance with one or more embodiments, the shield may extend coaxially around a perimeter of the loop antenna, i.e. shield and antenna are co-axially arranged.

In accordance with one set of embodiments, the antenna may further be for generating the electromagnetic excitation signals for propagation into the medium, and wherein the device further comprises a signal generation means adapted in use to drive the antenna to generate the excitation signals.

In this set of embodiments, the same antenna is used to generate the electromagnetic excitation signals as is used to sense signals returned from the medium in response.

This carries advantages in terms of functionality. In particular, as will be explained below, sensing of electromagnetic signals can readily be achieved by measuring reflected inductance components in the loop antenna via detuning of resonance characteristics of the coil. This simple method of signal analysis becomes possible only when the same antenna is used for sensing as for signal generation.

By 'driving' may be meant exciting the antenna.

By 'driving' may be meant driving an (alternating) current through the antenna such as to stimulate generation of oscillatory electromagnetic signals (waves).

The signal generation means may comprise a driver, e.g. an oscillator, for driving the antenna at a given frequency.

In accordance with one set of advantageous embodiments, the inductive sensing device may be adapted to generate the electromagnetic excitation signals with a radial frequency ω for propagating into said medium,
wherein a normalized radial frequency $$\hat{\omega} \equiv \frac{\omega}{\omega_{ref}}$$

of the electromagnetic excitation signals is from 0.025 to 0.50, where $\omega_{ref}=2\pi c/l$ and c=the speed of light and l is a circumferential length of a single winding of the loop antenna. For the avoidance of doubt $c=3\times10^8$ m/s.

This set of embodiments is based on results of a significant program of research undertaken by the inventors by which it has been found that the above parameter of normalized radial frequency $\hat{\omega}$ of the electromagnetic excitation signals is the most important parameter in determining the strength of the signal sensed by the device.

More particularly, research has found that at values of $\hat{\omega}$ below 0.025, the signal to noise ratio of the sensed electromagnetic signal is significantly reduced, leading to higher motion sensitivity. More particularly, below this level, the signal strength is much decreased, and in most practical applications saturated by noise emanating from electronic noise, electromagnetic interference and noise from capacitive coupling with the surface of the medium (i.e. direct coupling via electric fields and electrically induced charges).

However, despite the highly significant signal strength advantages which the inventors have found, frequencies as high as those claimed have never been explored in the state of the art. This is most likely due to a strong prevailing belief in the field that (absolute) frequencies above around 10-29 MHz lead to a significant reduction in achievable penetration depth due to skin effects. The assumed penetration depth reductions would render the system ineffectual for probing physiological parameters. The inventors however have found that this prevailing prejudice is a misconception, as even though the skin effect is real, it becomes only significantly detrimental at much higher frequencies than those used in the present invention.

It has further been found that a value of 0.50 for $\hat{\omega}$ is the highest that is physically possible while still achieving effective inductive sensing. This is the highest possible normalised frequency of the first resonance of a (single) loop antenna, which is the resonance at which precisely half a wavelength fits around the circumference of the loop.

Above the first resonance, a highly non-uniform current is induced in the loop, and the loop will carry a stationary oscillating pattern of accumulated charges. This fringe pattern of accumulated charges will typically capacitively couple to the surface of the medium, thereby inducing surface charges on the surface of the medium.

In this case, the sensor is rendered highly sensitive to motion of the medium surface, where even very small movements induce parasitic signals which fully drown out the inductive signal being sensed (namely the magnetic inductive signal originating from beneath the surface of the medium). This renders the inductive sensor ineffective for most practical applications. Hence, by keeping $\hat{\omega}$ below a value of 0.5, signal strength can be maintained at a level suitable for practical applications.

The range of values for $\hat{\omega}$ provided by the present invention therefore maximise the signal strength achievable in inductive sensing. It shall be also understood by the skilled person that the inductive sensing device described in this application can also work in an optimized way, when in the loop is placed in a medium. In this case $\omega_{ref}=2\pi V_p/l$, where $V_p$ is the phase velocity of light in the medium surrounding the loop when it is used.

In accordance with one or more examples, the antenna may be a single-turn loop antenna. It has been found in the course of investigation that, contrary to expectation, increasing the number of coil windings (coil turns) N above one (a single loop) provides no detectable improvement in signal strength. Moreover, increasing the number of windings is in fact detrimental to the object of maximizing signal strength because increasing the number of windings limits the maximum realizable value of $\hat{\omega}$ due to capacitive coupling between the windings. This in turn restricts the available increase in signal strength.

The two features of the above defined $\hat{\omega}$ range and the single coil antenna are therefore fundamentally interrelated. Where the antenna comprises more than a single turn (N>1), the maximum frequency $\hat{\omega}$ that can be used with the loop is significantly reduced below $\hat{\omega}=0.5$ due to parasitic capacitances between the loops and the longer total length of the coil wire Nl. This makes achievement of the beneficial normalized frequency range claimed in the present invention, and the accompanying increases in signal strength, impossible. Hence, only by reducing the number of coil windings to one are the beneficial higher $\hat{\omega}$ values possible.

However, restricting the coil windings to one is contrary to prevailing assumptions in the art, which generally assume that multiple coil windings increases signal strength by enhancing the flux linkage. This has further contributed to the reluctance in the field to explore frequencies in the range presently claimed.

Multiple windings also add costs and complexity to the sensor. Reducing to a single loop simplifies construction and operation of the device and reduces form factor.

More detailed physical explanation and grounding of the particular range identified will be presented below. In brief however, the claimed set of embodiments is based on the finding that reflected inductance (inductance of the antenna resulting from eddy currents induced in the medium in response to electromagnetic stimulation) is the key determinant in the resulting received signal strength at the antenna. By first normalizing this quantity, so as to render it effectively dimension-independent, and then simulating variation of various parameters upon which it is dependent, normalized radial frequency of the sensed signals was found to be the most significant parameter in determining reflected inductance. The optimal range of values for $\hat{\omega}$ claimed in the present application was then identified.

Electromagnetic excitation signals having a radial frequency ω may be generated by exciting the antenna at a radial frequency of ω. By this may be meant exciting the antenna so as to resonate at a frequency of ω. By this may in particular be meant inducing in the antenna a resonating current having radial frequency ω.

This may be achieved by providing an antenna circuit having a natural resonance frequency equal to ω. The natural resonance frequency of the antenna may be set by providing a capacitor coupled to the antenna and appropriately selecting the capacitance of the capacitor. The combination of antenna and capacitor is known as a resonator.

Additionally or alternatively, exciting the antenna so as to induce in the antenna a resonating current having radial frequency ω may be achieved by exciting the antenna with a current of frequency ω.

The normalized radial frequency $\hat{\omega}$ of the electromagnetic excitation signals is dependent upon the radial frequency ω of the electromagnetic excitation signals and the reference frequency $\omega_{ref}=2\pi c/l$ of the antenna (which is the radial frequency at which the loop circumference l equals one free-space wavelength (i.e. where $\lambda_{free\ space}=l$)).

Hence embodiments of the invention may require that the antenna and/or a capacitor and/or signal generation means are together configured such that the normalised radial frequency is within the defined range By way of example, this may be achieved for instance by providing a capacitor coupled to the antenna and selected such as to set the natural resonance frequency of the circuit at $\omega$, and choosing an antenna with the correct circumferential length l. Where the circuit has a given natural resonance frequency, it may be induced to resonate at that frequency by exciting it, for instance using a free-running oscillator (one without a fixed or forced oscillation frequency).

In accordance with one or more embodiments, the device may comprise a signal processing means adapted to process signals received at the antenna and to downscale a frequency of the signals by mixing each signal with a reference oscillatory signal of a different frequency, and apply a differential filter to derive an output signal having a frequency being the difference between the frequency of the oscillatory signal and the received signal.

The object of such embodiments is to reduce energy consumption and required computing power of any signal processing performed by the device. In particular, digital dividers and counters (for processing the received signals for analysis) draw current proportional with the operating frequency. Hence, to save power, in accordance with the present embodiments, the frequency of the received signals is first reduced, allowing the subsequent signal processing to be performed at lower power.

The advantage of the particular method proposed, of first mixing a second signal and then finding a differential frequency signal, is that mixing does not result in a loss of resolution. This is in contrast for instance to dividers (which can also be used to reduce frequency) which do reduce resolution.

The oscillatory signal frequency is preferably very close to the frequency of the received signals. In preferred examples, the frequency of the oscillatory signal and the frequency of the received signals are from 10 to 20% apart.

As explained above, the received signals will typically have frequency equal to $\omega$, i.e. the radial frequency of the electromagnetic excitation signals.

Examples in accordance with a further aspect of the invention provide an inductive sensing method for sensing electromagnetic signals emitted from a medium in response to propagation into the medium of electromagnetic excitation signals, the method comprising:

using a loop antenna to inductively couple with the electromagnetic signals emitted from the medium in order to sense said signals, wherein a blocking shield is arranged in a propagation path of the antenna for intercepting electromagnetic signals propagating to or from the antenna, the shield comprising an electrically conductive body for blocking electrical components of incident signals, and wherein the body delimits one or more non-conductive gaps for inhibiting induction of eddy currents within the body and wherein a loop of the antenna is broken by an opening, the opening being bridged by a capacitor, and wherein a signal processing means is electrically coupled to the antenna via only a single point of the antenna, located to one side of the opening.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a magnetic inductive sensing device comprising a loop antenna for inductively coupling with electromagnetic (EM) signals emitted from a medium in response to stimulation of the medium with electromagnetic excitation signals. The device includes an electromagnetic shield element which is arranged such as to intercept electromagnetic signals travelling to or from the antenna. The shield element is formed of conductive material such as to block electrical field components of incident signals but further incorporates a non-conductive gap in the material so as to prevent the formation of eddy currents. A loop of the antenna is broken by an opening, the opening being bridged by a capacitor, and the device comprises a signal processing means which is electrically coupled to the antenna via only a single point of the antenna, located to one side of the opening.

By inhibiting eddy current formation in the body of the shield, oppositional magnetic fields are not induced by the shield upon incidence of magnetic field components of EM signals. The magnetic field components are not therefore cancelled out by such fields and the components are thus not blocked by the shield.

In this way the shield blocks electric field components, but passes magnetic field components, reducing electric field noise in the sensed magnetic inductive signals and improving signal to noise ratio.

Embodiments of the present invention operate on the principle of inductive coupling, whereby a coil or wire has induced across it a potential difference due to exposure to a time-varying magnetic field. Embodiments of the present invention use this principle to measure strength of electromagnetic signals generated within regions of a medium or body by sensing changes in characteristics of a current generated in a loop antenna placed in proximity of the body. In preferred examples, changes in the inductance of the coil are sensed, where these changes are detected for instance based on changing resonance characteristics of the coil circuit.

In embodiments, a loop antenna is used to sense electromagnetic signals emitted by a body in response to an electromagnetic excitation signal that is emitted into the body. In advantageous examples, the same coil antenna may be used to generate the excitation signals as to sense the returned electromagnetic signals.

Figure 1:
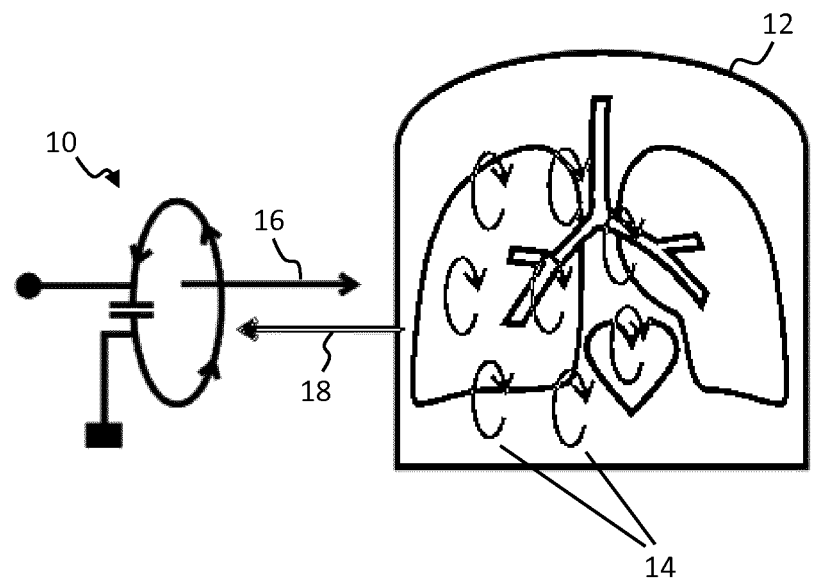
FIG. 1 shows stimulation of a thorax of a subject using a loop antenna.

This principle is illustrated schematically in FIG. 1, which shows by way of example a loop antenna 10 being driven with an alternating current in proximity to a thorax 12 of a subject, so as to propagate electromagnetic signals 16 into the thorax.

As a consequence, eddy currents 14 are induced within in the thorax. The eddy currents naturally arise due to Faraday's law of induction, whereby an electromotive force (EMF) is induced in a conducting medium in response to presence of a time-varying magnetic field.

The eddy currents in turn result in generation of a time-varying magnetic flux 18 of equivalent frequency to that generated by the primary antenna 10. These fluxes result in propagation of electromagnetic waves (signals) 18 which can be sensed at the antenna 10.

In accordance with advantageous examples, the system may be used for sensing physiological parameters and properties, for instance air, fluid and/or tissue movements in the body of a subject. The system may be advantageously applied in particular for sensing breathing movements for instance.

In these examples, the system senses air, fluid and/or tissue movements (e.g. caused by breathing or the beating of the heart) by sensing modulations in the reflected inductance of the signal caused by these movements.

It will be appreciated that movements of tissue in the body can comprise changes in volume of the tissue. These modulations cause amplitude and/or phase modulations of the electromagnetic signal.

A modulated electromagnetic signal is emitted by the body in response to the electromagnetic excitation signal that is emitted into the body of the subject. As the tissue, air or fluid move or expand and contract, the eddy currents generated in the medium change shape and form resulting in modulation of the returned EM signals. This allows sensing of changes and movement beneath the surface of a body.

Magnetic fields penetrate deeper into a body than electric fields, and thus magnetic fields can be used to measure changes in properties deeper inside the body, whereas electric fields can be used to measure changes in properties on the surface of the skin, e.g. the permittivity of the skin. Thus, properties of the antenna 10 and the generated electromagnetic excitation signals are preferably configured such that the antenna is most sensitive to magnetic signals (magnetic components of the electromagnetic signals) and minimally sensitive to the electric signals, i.e. such that the magnetic field behavior of the emitted electromagnetic signal dominates over the electric field behavior.

Embodiments of the present invention thus provide a new shielding approach allowing shielding of the antenna to electric fields, while allowing passage of magnetic fields.

The shielding concept will now be explained.

The electromagnetic field around a coil or antenna is characterized by a near-field region and a far-field region. The near field region is typically defined by the distance of one wavelength, $\lambda$, divided by $2\pi$. For relatively high frequency electromagnetic signals of 400 MHz (which is within a preferred range of values used in accordance with certain embodiments to be described below), this corresponds to a distance of 0.12 m. Hence where the antenna is intended to be held within around 0.12 m of the body to be investigated, the near-field region is the only region of concern. Such distances are the case for instance for on-body sensing applications, such as wearable sensors for instance. Changes of material properties (i.e. local blood volume fluctuations) in the near field region can be typically seen as a change in the loop impedance. This changing impedance can be measured in several ways, such as by the use of a phase-locked loop.

To enable inductive sensing of such changes in material properties, including for instance sensing of vital signs in accordance with certain advantageous embodiments, it is advantageous, as discussed above, to suppress the detection of undesired electric fields resulting from surface charges in the biological tissue (from electrostatic induction). These electric fields are unwanted as they do not carry information on materials beneath the surface of a body or medium (as they originate from the body surface). However, they also readily dominate the electromotive force induced by the eddy currents 14 inside the body (which do carry information on internal properties).

Electrostatic induction readily occurs in cases of physiological sensing for instance because the relative permittivity of biological tissues is approximately $\varepsilon_r = \sim 70$, which is much larger than 1.

Figure 2:
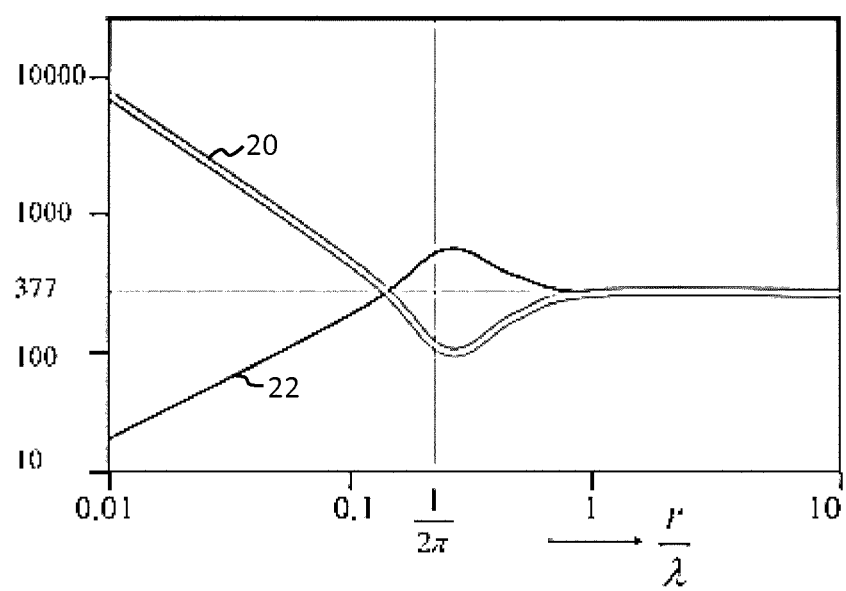
FIG. 2 compares wave impedance for electromagnetic waves travelling to or from a shielded and an unshielded antenna.

Wholly unshielded antennas will output electromagnetic field signals with relatively high field-impedance (i.e. high ratio of transverse electric to magnetic field components). By contrast, a shielded antenna will output a relatively low field-impedance signal (i.e. low ratio of transverse electric to transverse magnetic field components). This is illustrated in FIG. 2, which shows the field-impedance (y-axis) as a function of distance (normalized by wavelength) from the antenna (x-axis: distance divided by $\lambda$, in meters) for two fields, one (line 20) generated by an unshielded antenna, and a second (line 22) generated by a shielded antenna.

The high electric field component of the unshielded antenna signal 20 will cause electrostatic induction. In addition, the unshielded antenna will be sensitive to the resulting unwanted electric fields reflected back. By contrast the low-impedance field of the shielded antenna will result in little electrostatic induction and not be sensitive to returning electric field components of signals.

Figure 3:
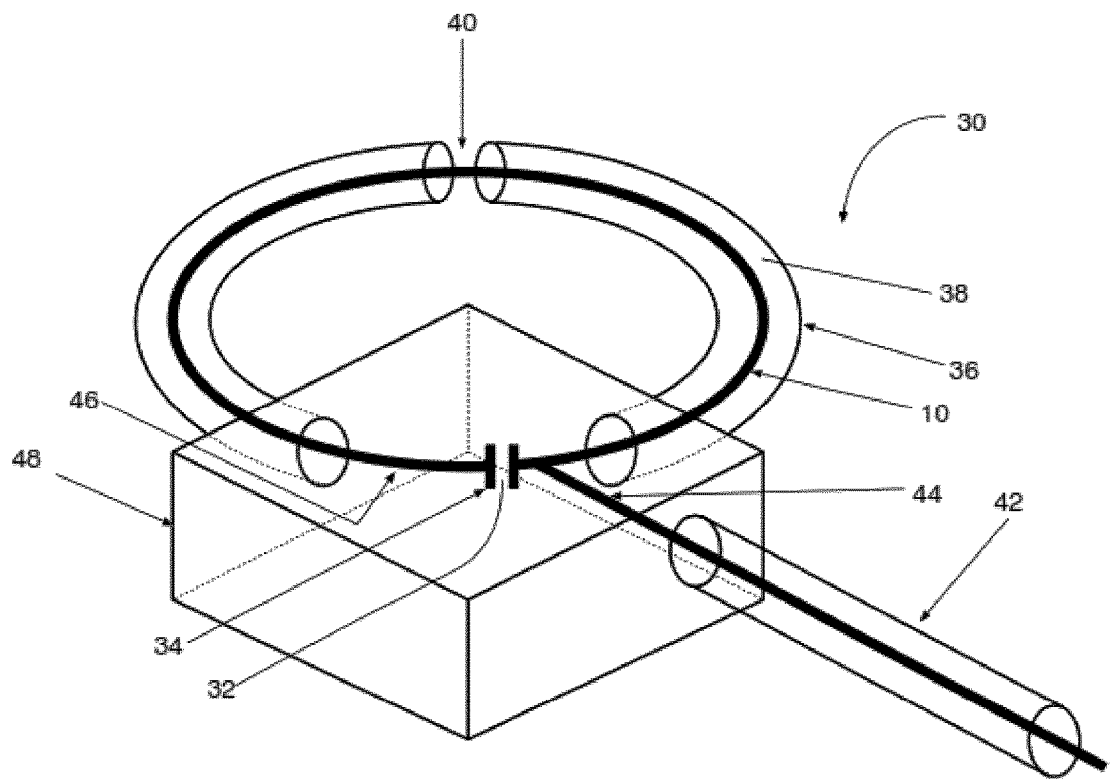
FIG. 3 shows an example sensing device in accordance with an embodiment.

An example magnetic inductive sensing device in accordance with an embodiment of the invention is shown in FIG. 3.

The device 30 comprises a loop antenna 10 having a single-turn wire loop. The antenna is broken by an opening, the opening 32 being bridged by a capacitor 34. The capacitor may be chosen such as to tune the antenna circuit to a desired resonant frequency.

The antenna 10 is coaxially surrounded by an electromagnetic shield 36 element. The shield comprises an outer conductive shell or wall which provides the shielding function and forms a tubular element which surrounds the antenna. The outer conductive shell forms a conductive body of the shield. Between the outer conductive wall and the antenna is a dielectric (i.e. insulating) medium 38 which also acts to mechanically secure the antenna and outer shell in fixed positional relationship.

The shield thus provides a Faraday shield. A gap 40 is formed in the circumference of the shield, the gap extending radially through the shield body from outside to inside the shield circumference.

The shield 36 is thus configured such that the gap formed through it is aligned so as to cross the circumference of the antenna 10 loop. The gap in this case circumferentially surrounds the portion the antenna loop exposed by the gap.

The shield 36 is thus arranged relative the antenna 10 such that electromagnetic signals emitted from the antenna and electromagnetic signals travelling to the antenna are intercepted by the shield.

Upon incidence at the shield 36 of electric field components of electromagnetic signals, the field interacts with electric charges within the shield's body 38. This interaction shortens the electric fields, and inhibits their further propagation.

Upon incidence at the shield 36 of magnetic field components of electromagnetic signals, the oscillating magnetic flux has a current inducing effect within the conductive material of the outer wall of the shield 36. Typically, this would manifest in formation of eddy currents circulating at the surface of the shield body which in turn generate oppositional magnetic fields and cancel out the incident field components. However, the presence in the shield body of the non-conductive gap 40 inhibits formation of such eddy currents. Hence, the shield does not block passage of magnetic field components.

The overall effect is that the shield blocks electric field components of incident electromagnetic signals, while passing magnetic field components. Thus the electric field noise in the signal received at the antenna 10 is reduced and signal to noise ratio of the magnetic inductive sensing device is improved.

Although the particular example of FIG. 3 comprises a capacitor coupled to the antenna, a capacitor is not essential to the inventive concept.

The device may further comprise a signal processing means for processing electromagnetic signals received at the antenna, such as signal processing circuitry or a microprocessor or a micro-controller. Alternatively, the antenna may be configured to be coupled to an external signal processing means.

In either case, according to the example of FIG. 3, the signal processing means electrically coupled to the antenna 10 via connecting coaxial wire 42 which inner conductor is connected to the antenna by only a single connection point 54, located on one side (one wing) of the opening 32 in the antenna loop. An outer conductor of the coaxial wire is electrically connected to the shielding 36 via box 48. The other side of the antenna loop is connected to the signal processing means only via the bridging capacitor 34. Accordingly, the signal processing means is coupled to the antenna only loosely which advantageously avoids heavily loading the signal processing means.

The device 30 further comprises a secondary shielding element 48 in the form of a shielding box which is arranged enclosing a sub-portion 46 of the antenna loop. The shielding box is formed of a conductive material to inhibit passage of electromagnetic signals. The shielding box thus forms a Faraday shield.

An outer wall of the shielding box is electrically connected to the coaxial shield 36 and spaced from the antenna 10 by air.

The shielding box encloses both the bridging capacitor 34 and the connection point 44 of the signal processing means (via wire 42) to the antenna 10 loop. There is thus provided a more electromagnetically stable environment surrounding these components of the device.

The location of the non-conductive gap(s) in the shield can be varied such as to optimally balance the magnetic field.

In use, the antenna 10 and shield 36 arrangement is held in proximity to a medium or body of interest. Electromagnetic excitation signals are propagated into the body to stimulate formation of eddy currents 14 (as discussed above with reference to FIG. 1) and the antenna of the device inductively couples with magnetic field components of electromagnetic signals emitted back from the body in repose to said excitation. The shield 36 blocks passage of electric field components of the signals and (due to the non-conductive gap 40) permits passage of magnetic field components. Thus the antenna is able to inductively couple with magnetic signals.

Signal processing means may then process the received signals in order to derive information concerning the body or medium stimulated. The signal processing means may be adapted to analyze an inductance of the antenna 10 loop in order to sense the received signals.

The antenna loop 10 and capacitor form a resonant circuit having a natural resonant frequency. The shield 36 with gap 40 also has a natural resonant frequency. Preferably, the resonant frequency of the shield is higher than the resonant frequency of the antenna and capacitor circuit. The gap (40) may preferably be made a small as possible, but while maintaining a higher resonant frequency of the shield than of the antenna and capacitor.

In preferred embodiments, the antenna 10 of the sensing system both generates the electromagnetic excitation signals which are propagated into the body or medium and senses electromagnetic signals returned from the medium due to formation of eddy currents.

To this end, the device 30 may further comprise signal generation means for driving the antenna to generate electromagnetic excitation signals. The signal generation means may for instance comprise a driver unit adapted to drive an alternating or other periodic current through the antenna 10 loop to stimulate generation of electromagnetic emissions from the antenna. The signal generation means may for instance comprise an oscillator for driving the antenna.

Signal processing and generation methods will be described in greater detail to follow.

The loop antenna 10 is preferably driven at a relatively high frequency (e.g. in the order of 0.1 to 1 GHz) to create a stable electromagnetic environment.

The number of windings of the antenna 10 is preferably kept small, to minimize capacitive effects between the wires. Although the example device of FIG. 3 features an antenna with only one winding, this is not essential and the antenna may comprise more windings in other examples.

It is preferable to keep the current distribution over the antenna as even as possible. The current distribution over the loop may be assumed to be approximately even provided the circumference of the loop is less than approximately 1/10 of the wavelength of the incident electromagnetic signals (and emitted electromagnetic excitation signals, where the antenna is thus used).

The resonance of the tuned antenna 10 circuit occurs between the inductive loop 10 together with the bridging capacitor 34 (and also the (comparatively lower) capacitance between the antenna 10 and shield 36). The inductance of the loop is dependent on the loop circumference.

Figure 4:
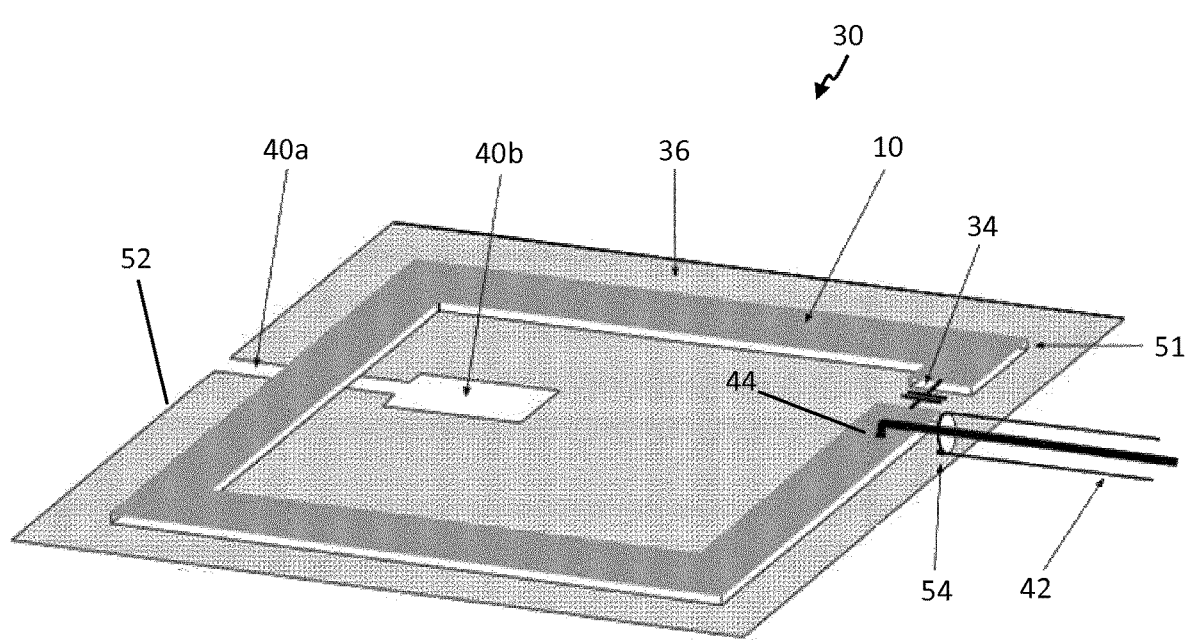
FIG. 4 shows a further example sensing device in accordance with an embodiment.

A second example magnetic inductive sensing device in accordance with one or more embodiments of the invention is shown in FIG. 4. This example device 30 has a flat structure, as opposed to the coaxial tube-like structure of the example of FIG. 3. This may render it suitable for instance for wearable applications.

The device 30 comprises a shield 36 in the form of a plate element, in particular a planar ground plate. The plate element forms a conductive body of the shield. The ground plate features a gap 40 in the form of a slot extending inward from an edge 52 of the plate approximately to a central point of the plate. The gap in this example has a smaller width portion toward the edge 52 of the shield, and a larger width portion toward the middle of the shield. In other examples however, the slot may have uniform width along the whole of its length.

A loop antenna 10 in the form of a single rectangular tuned loop is provided disposed above the shield 36 in co-planar fashion, the two separated by a small clearance in the order of for instance tens of micrometers. The shield is thus arranged facing one planar side of the shield. The loop is formed by a solid non-conductive carrier disposed with a conductive top layer. The loop in this example extends in a rectangular annular fashion to define the loop. In other examples however, the loop may be any annular shape, e.g. rounded, such as circular or oval.

The conductive top layer of the antenna loop 10 may be in the form of a thin flat conductive foil.

The ground plate 36 is arranged such that the gap 40 is aligned crossing the circumference of the antenna 10 loop.

As in the example of FIG. 3, the antenna 10 loop is broken by an opening which is bridged by a capacitor 34. The capacitor may be chosen such as to tune the antenna circuit to a desired resonant frequency.

The antenna 10 is coupled to the ground plate 36 via a co-axial feed line provided by an outer conductor of a co-axial wire 42. The ground feed point of the outer conductor to the shield is indicated schematically by point 54. An inner conductor of the co-axial wire 42 is electrically connected to the conductive upper layer of the antenna loop 10 by the connection point 44. The co-axial wire provides connection to a signal processing and/or generation means for analyzing sensed signals and/or driving generation of outgoing excitation signals.

To optimize the impedance match of the antenna 10 to a signal processor or signal generation means, the location of the ground connection 54 can be changed. The voltage-current relation changes along the length of the antenna loop, thus enabling the electrical properties of the connection to be adjusted. In particular, the antenna has an impedance at resonance frequency which varies with the distance to capacitor 34. The impedance drops as a function of increasing distance.

The antenna 10 is isolated from the grounded shield 36 by an insulating or dielectric layer 51.

In contrast to the sensing device of FIG. 3, the example of FIG. 4 provides a flat antenna with a flat, planar shield arranged on one planar side of the antenna. Surprisingly, it has been found through experiment and simulation that the shield in this arrangement is just as effective in its shielding function as the arrangement of FIG. 3 comprising both a co-axial shield which completely surrounds the antenna loop and a secondary shielding box 48. This is especially the case where the thickness of the non-conductive carrier track of the antenna loop is small, for instance a few millimeters.

In use, the arrangement 30 is held such that the shield is disposed between the antenna and the body being probed, i.e. in the propagation path between the antenna and the body under investigation. The shield blocks propagation of electric field components of outgoing and incoming electromagnetic signals while allowing magnetic field components to pass.

Although shield 36 is in the form of a rectangular plate in the example of FIG. 4, this is by way of example only. In further examples, one or both of the shield and antenna 10 may instead be round for instance, provided that the gap 40 in the shield 36 is aligned such as to cross the antenna 10 circumference.

The structure may in examples be advantageously formed from printed circuit board (PCB) material using commonly used production techniques.

In accordance with further examples, the arrangement of FIG. 4 may be adapted to include a further coupling capacitor provided between the grounded plate shield 36 and the antenna 10.

Figure 5:
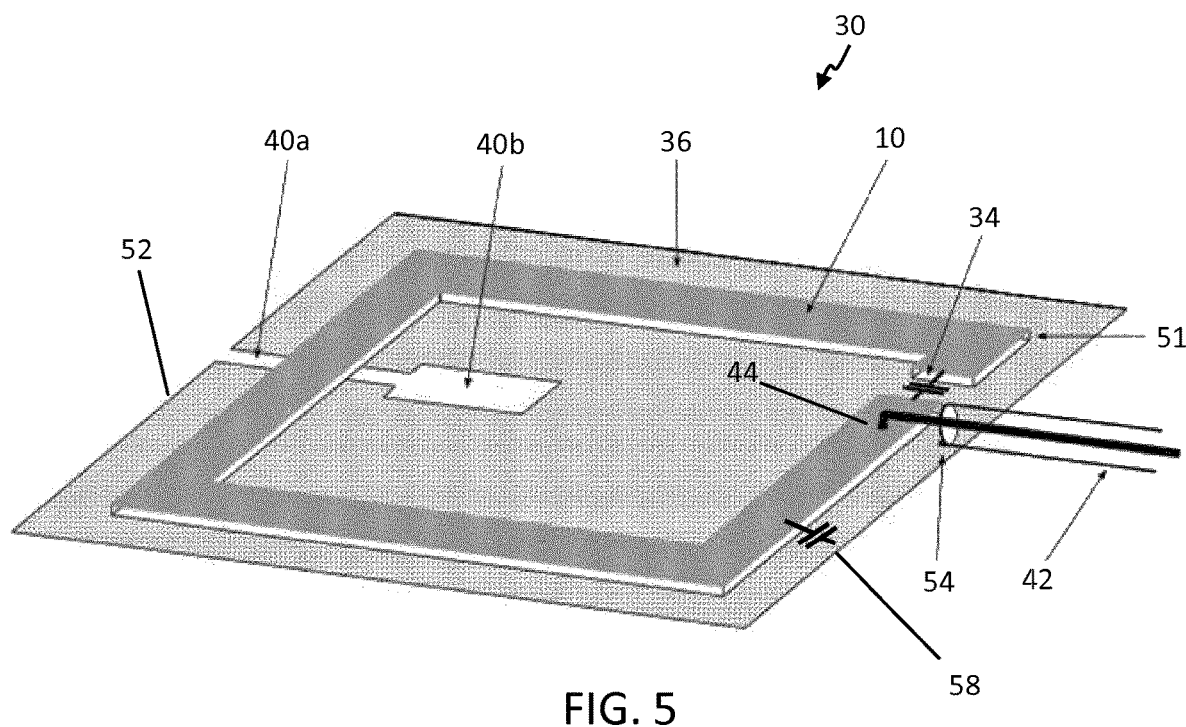
FIG. 5 shows a further example sensing device in accordance with an embodiment.

An example of this variant is shown in FIG. 5. The device 30 of this example is the same in all respects as the example of FIG. 4 except for comprising an additional tuning capacitor 58 which is provided electrically coupling the shield ground plate 36 and the antenna 10.

The capacitor provides a further means for optimizing the impedance matching between the ground plate shield 36 and the antenna 10 (in addition to adjusting the location of the connection point 54 between the shield and the antenna). By adjusting the capacitance, the impedance matching can be optimized.

The flat shielded antenna device 30 of FIG. 5 has been tested in the lab. The device was shown to provide much more stable sensing behavior due to the controlled electromagnetic environment provided by the plate shield.

The performance of the device in measuring various vital signs was tested. The detected signal strength was significantly improved compared to known unshielded antenna.

Figure 6:
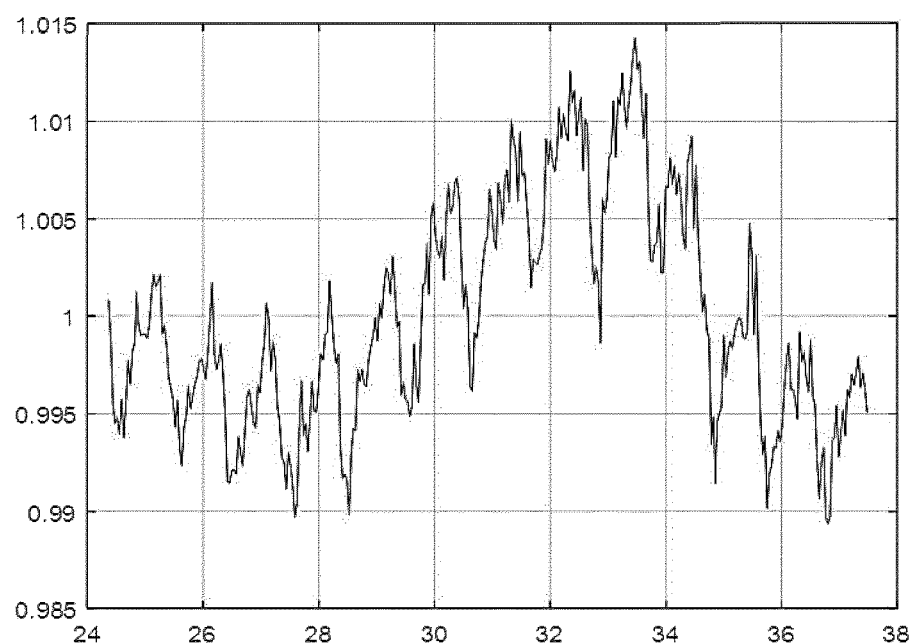
FIGS. 6 and 7 show sample physiological measurement signals obtained using an example sensing device.
Figure 7:
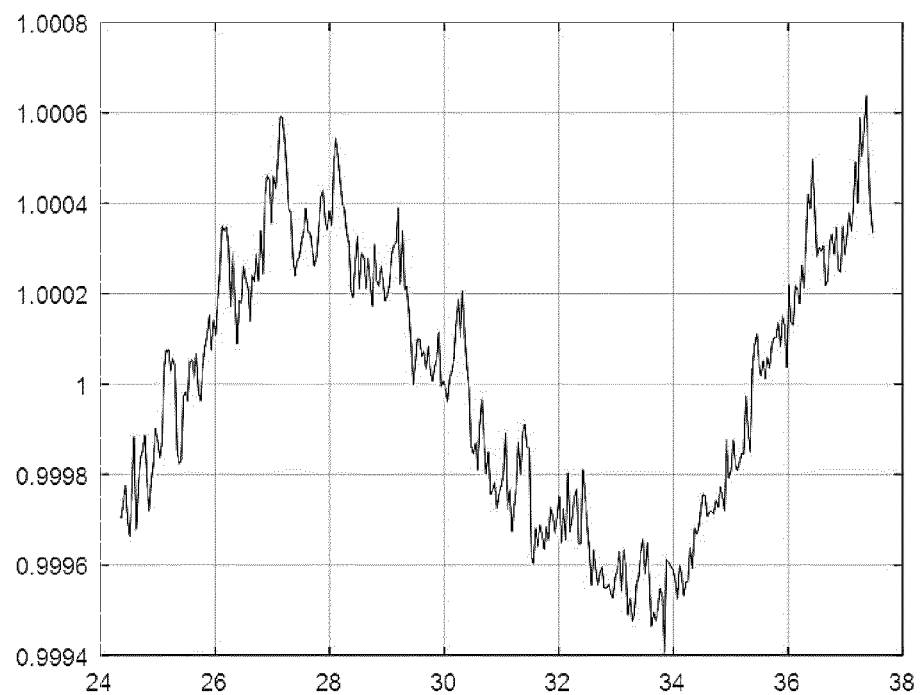

Examples of the obtained results are shown in FIGS. 6 and 7. FIG. 6 shows the signal obtained for measurement of a subject's heartbeat and breathing, by placement of the sensing device of FIG. 5 in proximity to the subject's chest. The obtained signal is shown as variation of the antenna normalized loop inductance (y-axis) as a function of time (x-axis, seconds). It in particular shows the normalized imaginary part of the antenna impedance, translated into the normalized inductance of the antenna loop, measuring heart beat and respiration of a person.

FIG. 7 shows the signal obtained for measurement of a subject's heart beat and breathing using the sensing device of FIG. 5, placed proximal to a subject's chest. The antenna was driven at a frequency of 230 MHz to generate the excitation signals propagated into the subject's body. The signal shows variation of the normalized resistance of the antenna, i.e. normalised real part of the antenna impedance (y-axis) as a function of time (x-axis, seconds).

Figure 8:
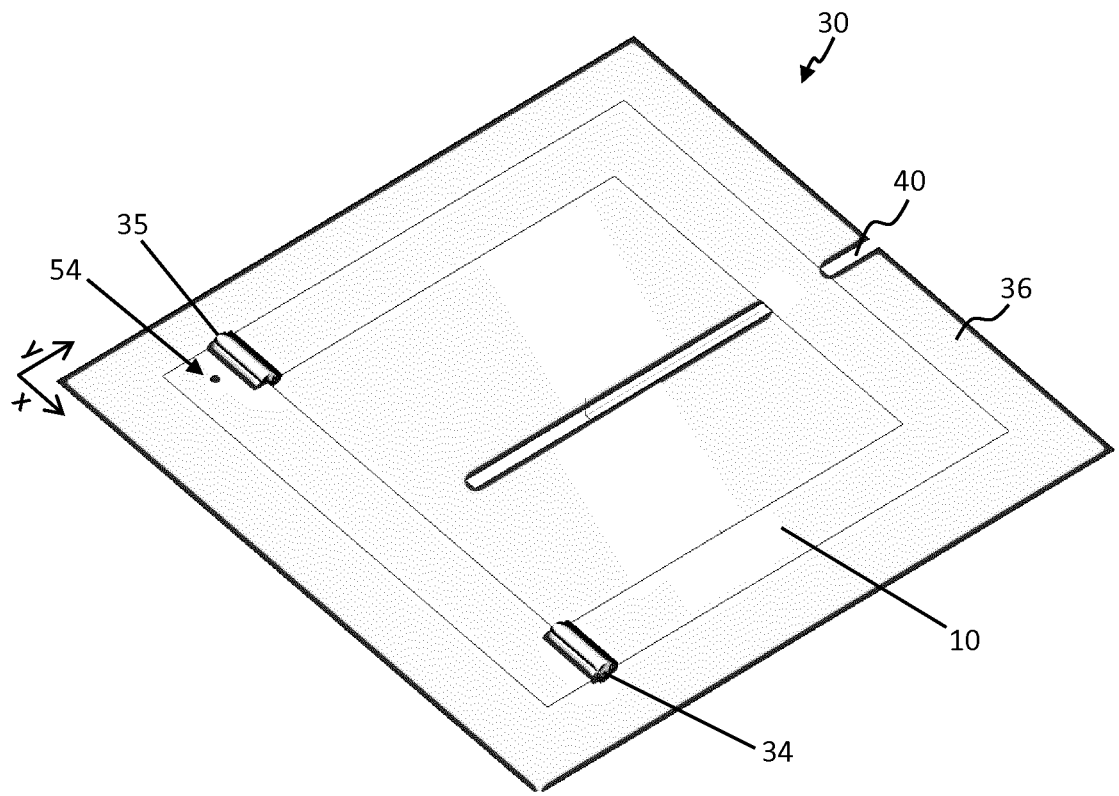
FIG. 8 shows an example sensing device in accordance with an embodiment.

A further example sensing device is shown in FIG. 8. The arrangement is similar to that of FIG. 4. The device 30 comprises a shield 36 in the form of a ground plate. A loop antenna 10 is disposed in co-planar fashion above the shield 36, separated from it by a small clearance which may be filled with an insulating (i.e. dielectric) material. In this example, the spacing between the antenna and the shield is 1 mm.

A gap 40 is provided in the shield 36 in the form of a narrow slot which extends inwards from an edge of the shield plate 36, and through a center point of the shield plate. The slot in this example is 1 millimeter wide and 25 millimeters long.

The loop antenna in this example has total outer dimensions of 35 millimeters×35 millimeters (core line), with a width of the annular antenna loop of 5 millimeters.

All dimensions are purely exemplary, and in other examples, different dimensions and distances may be used.

The loop antenna 10 is broken by two openings, each of which is bridged by a respective capacitor 34, 35. The capacitors enable tuning of the antenna circuit in order to bring the system to resonance. In the present example, capacitors were provided giving a total capacitance to the antenna system of 3 to 15 picoFarads.

The loop of the antenna is preferably significantly smaller than the wavelength of the electromagnetic signals generated by the antenna, or the signals to be received by the antenna. In the particular example of FIG. 8, the circumference was provided at a length of one quarter of a wavelength of the utilized EM radiation.

In accordance with any embodiment, the sensing device may be operated in the following way.

The tuning capacitor 34 of the antenna, in combination with the electrically coupled antenna 10, form a resonator circuit. The natural resonance frequency of the resonator may be set by selecting the capacitance of the capacitor. The resonator may be controlled to generate electromagnetic excitation signals for propagation into a body by exciting the resonator with an oscillatory current. Exciting the resonator is performed by a signal generation means, for instance in the form of an oscillator. When the resonator circuit is excited, it resonates at its natural frequency (i.e. a resonating current is established flowing back and forth between the antenna and the capacitor). This drives generation of electromagnetic waves (excitation signals) having frequency equal to the frequency at which the resonator is resonating. Hence by appropriately selecting the capacitance, the frequency of the excitation signals may be set.

Electromagnetic signals returning from the body may be sensed by analyzing the signals using the signal processing means. In particular, the signal processing means may be adapted to detect changes in the natural frequency of the resonator circuit and/or the damping parameter of the resonator circuit. The magnitude of such changes provides an indication of the strength of the returning signals as the returning signals provide an extra component of inductance (reflected inductance) which leads to a detuning of the resonator circuit.

Advantageous embodiments of the sensing device preferably comprise a loop antenna whose circumference is significantly smaller than a single wavelength of the electromagnetic signals being generated and sensed (for instance equal to approximately a quarter of a wavelength). Preferably there is also provided one or more series capacitors which bring the total structure to resonance. This may alternatively be achieved by (a combination of) other electrical components.

Simulations have been performed to test behavior of the flat plate shield variant of FIGS. 4, 5 and 8. These tested the electric and magnetic field behavior on the bottom (shielded) side of the antenna arrangement and the top (unshielded) side of the antenna arrangement. It has been found that the bottom shielded side exhibits, via the gap 40, very strong magnetic field behavior and almost no measurable electric field activity. The top unshielded side exhibits weaker magnetic field behavior, and also some weak electric field behavior. It is clear therefore that the shield both blocks electric field components and enhances magnetic field components of electromagnetic signals.

In accordance with any embodiment of the invention, the gap 40 dimensions can be selected according to requirements. The larger the width of the gap, the greater the sensitivity of the antenna to incoming magnetic signals, since the inhibiting effect on formation of eddy currents in the shield is increased. However, at the same time, a wider gap also increases sensitivity of the antenna to electric field components, which can propagate through the gap, which is undesired. A smaller gap improves blocking of electric field components, but also slightly reduces sensitivity to magnetic field components of signals, since there is greater possibility of eddy currents forming in the shield (which counter incoming magnetic fields).

In most cases however, it is preferable to provide a gap which is small in width as the electric field components are more of an impediment to signal strength than the small reduction in magnetic sensitivity.

Above have been described the main features of example sensing devices provided by embodiments the invention, in particular relating to shielding of the antenna.

Any embodiment of the invention may be provided with accompanying circuitry for facilitating signal processing. Certain embodiments may further comprise circuitry for facilitating driving of the antenna for generating electromagnetic excitation signals for propagation into a body.

Figure 9:
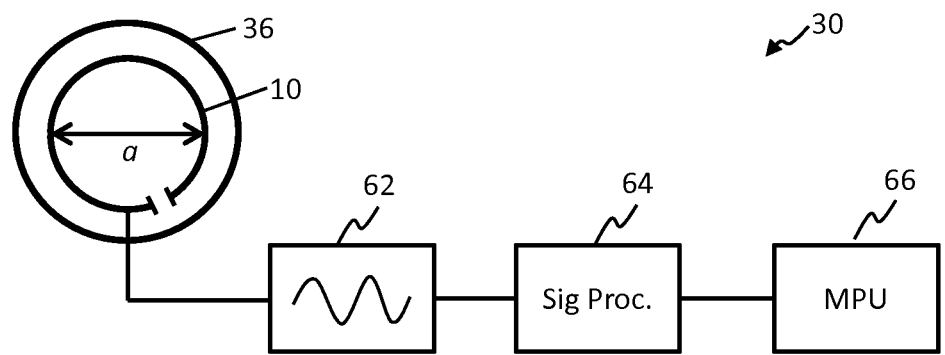
FIG. 9 shows example circuitry for an example sensing device according to an embodiment.

To illustrate, circuitry for one example magnetic inductive sensing device is schematically depicted in FIG. 9. The circuitry shown includes both signal processing and signal generation means. In further examples however, just one of the signal generation means or the signal processing means may instead be provided in isolation with the antenna.

The device 30 comprises a single-turn loop antenna 10, electrically coupled with a capacitor. This combined arrangement is known as a coil resonator. The antenna in this example is for generating electromagnetic oscillations or signals for propagation into a body and for inductively coupling with electromagnetic signals returned (or reflected) from the body in response to the excitation signals.

The antenna 10 is surrounded by a blocking shield 36 for intercepting electromagnetic signals propagating to or from the antenna. The shield arrangement may be in accordance with any of the examples or embodiments described above or below, or as defined any claim of the present application. The shield may for example be a planar sheet element such as in the examples of FIGS. 4, 5 and 8 or may for example be a co-axial shield element such as in the example of FIG. 3.

The loop antenna 10 is electrically coupled to a signal generation means 62 which is adapted in use to excite the resonator (antenna 10 and capacitor circuit) to generate the electromagnetic excitation signals. In accordance with the present example, the signal generation means is an oscillator which is configured to excite the antenna 10 with an oscillatory current in order thereby to generate a sinusoidal electromagnetic signal (a sinusoidal electromagnetic wave) for propagation into the body to be stimulated.

The antenna 10 is further electrically coupled to a signal processing means 64 ('Sig Proc.') in the form of a signal processing unit for processing the electromagnetic signals received at the antenna. In FIG. 9, the signal processing means is shown connected to the antenna via the signal generation means 62. However, this is not essential: the antenna and signal processing means may be independently connected.

The signal generation means 62 and signal processing means 64 may in examples be facilitated by a single unit. In accordance with particular examples, the functionality of both these elements is facilitated by a Vector Network Analyzer, containing an oscillator for exciting the resonator and impedance measurement means for sensing received signals.

The signal processing unit 64 analyses the characteristics of the response signal received at the antenna 10. In particular, the signal processing unit may process received signals to derive a measure of changes in the damping factor of the resonator circuit and/or the natural frequency of the resonator circuit, When electromagnetic signals are received back at the antenna they detune the characteristics of the resonator circuit, and this allows the received signals to be measured.

The system 30 also comprises a microcontroller 66 ('MPU') for controlling components of the system. For instance, the microcontroller may control the particular drive scheme implemented by the signal generation means 62 in driving the antenna and/or the particular analysis processes implemented by the signal processing means 64 and/or may control the sequence of driving and analysis operations. The microcontroller is optional however.

There may further be provided data communication means (not shown in FIG. 9) for facilitating communication between the microcontroller and an external device such as an external computer or data store. This may facilitate communication of signal processing results derived by the signal processing means to an external computer. It may also facilitate communication of control commands to the microcontroller 66 from an external control means such as a computer.

The data communication means may comprise a wireless communication means or wired communication means. The communication means may implement or operate in accordance with any suitable communication protocol or medium such as for example Bluetooth, Wi-Fi, Near Field Communication (NFC), ZigBee, or any suitable wired communication protocol.

In use, the antenna 10 is held in proximity to a body or medium of interest, with the shield arranged in the propagation path between the antenna and the body, and the antenna is excited by the signal generation means 62 to generate electromagnetic excitation signals.

In accordance with advantageous examples, the device may be used for sensing physiological parameters and properties, for instance air, fluid and/or tissue movements in the body of a subject. The system may be advantageously applied in particular for sensing breathing movements for instance.

In these examples, the system senses air, fluid and/or tissue movements (e.g. caused by breathing or the beating of the heart) by sensing modulations in the reflected inductance of the signal caused by these movements.

It will be appreciated that movements of tissue in the body can comprise changes in volumes of local regions of the tissue, as well as changes in conductive and dielectric properties of the tissue. These modulations cause amplitude and/or phase modulations of the electromagnetic signal.

A modulated electromagnetic signal is emitted by the body in response to an electromagnetic excitation signal that is propagated into the body of the subject. As described above, and illustrated in FIG. 1, the electromagnetic excitation signal causes magnetic induction, i.e. the generation of eddy currents 14 in the tissue due to the application of an external magnetic field 16, and this eddy current/electromagnetic signal is modulated by the movements of air, fluid and/or tissue in the subject.

The electromagnetic excitation signal is generated by means of the resonator (comprising the antenna 10 and coupled capacitor), and the reflected electromagnetic signals (caused by the induced eddy currents) are sensed by the same antenna. This electromagnetic excitation signal is generated through exciting the resonator using the signal generation means 62. The resonator circuit will resonate (i.e. a resonating current will be established flowing back and forth between capacitor and antenna) at its natural frequency thereby generating electromagnetic excitation signals at this frequency. The natural frequency can be set by selecting the capacitance of the capacitor.

The signal generation means 62 may be adapted to drive the antenna 10 to generate the electromagnetic excitation signals with a radial frequency ω. Driving the antenna may comprise driving the antenna with a current having a frequency equal to w in order to thereby generate the EM signal of frequency ω. The current may be alternating or otherwise periodic (e.g. pulsed).

Driving the antenna may alternatively simply comprise exciting the resonator circuit with a free-running oscillator (i.e. one with no fixed or forced frequency). The resonator circuit will then oscillate at its natural frequency.

In accordance with an advantageous set of examples, the device 30 may be configured to generate electromagnetic excitation signals of a normalized radial frequency $$\hat{\omega} = \frac{\omega}{\omega_{ref}}$$

of f from 0.025 to 0.50, where $\omega_{ref}=2\pi c/l$, c=the speed of light, and l is the circumferential length of the antenna loop. For avoidance of doubt, $c=3\times10^8$ m/s.

The normalized radial frequency $\hat{\omega}$ depends upon both the circumferential length of the antenna 1 and upon the radial frequency ω at which the antenna 10 resonates. Hence the antenna, the capacitor, and/or signal generation means 62 in these examples may together be configured to realize excitation signals of a normalized radial frequency falling within the given range. In particular, the capacitor may be chosen to set the resonance frequency of the antenna circuit, thereby setting m, and the antenna chosen to set the circumferential length l.

For an antenna of fixed circumferential length 1 for instance, this requires that the antenna circuit be configured or controlled to resonate or oscillate at a frequency between ω=0.0125 l/πc and ω=0.25 l/πc.

In the case of a circular loop antenna of radius a, l is naturally equal to 2πa.

Driving the antenna within this range of frequencies has been found to significantly improve signal to noise ratio of the measured magnetic signals. This has been discovered through a significant program of research undertaken by the inventors.

In particular, it was found by the inventors that the key determinant in the strength of the obtained signal to noise ratio of sensed electromagnetic signals is the strength of the (normalized) reflected component of coil inductance Lr.

When the antenna 10 coil is brought into proximity with a body or medium, the inductance L of the coil acquires an additional reflected inductance component, Lr, arising due to the eddy currents induced in the stimulated body as a result of application of the excitation signals (described above in relation to FIG. 1). The eddy currents effectively make a contribution to the inductance of the loop antenna 10 because they themselves result in generation of a time-varying magnetic flux 18 of equivalent frequency to that at which the antenna is being driven. These eddy-current fluxes combine with the primary flux of the antenna, resulting in a greater induced back-EMF in the antenna, and hence a larger measurable effective inductance. The magnitude of the reflected inductance at the antenna is related to the strength of the electromagnetic signals received from the probed body.

Through a number of computational models, the inventors have found that the parameter $$\hat{\omega} = \frac{\omega}{\omega_{ref}}$$

is the strongest determinant of the strength of the measured characteristic (i.e. normalised) reflected inductance $\hat{L}_r$, where $$\hat{L}_r \equiv \frac{L_r}{2\pi a N^2} = \frac{L_r}{l N^2}.$$

Figure 10:
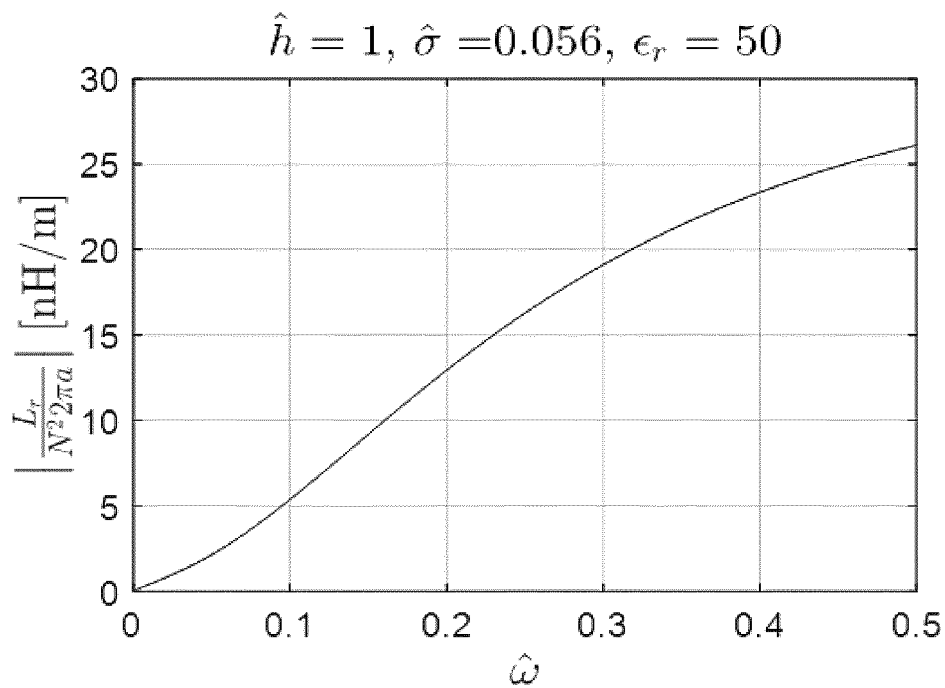
FIGS. 10 and 11 show modelled characteristic reflected inductance as a function of changing normalized radial operating frequency for an example sensing device in accordance with two different models.

FIG. 10 shows results of computational modelling of electromagnetic stimulation of a homogeneous medium using a single turn (N=1) coil of fixed radius a, at a fixed characteristic distance from the medium $$\hat{h} \equiv \frac{h}{a} = 1,$$

with fixed characteristic conductivity $$\hat{\sigma} \equiv \frac{\sigma l}{2\pi\varepsilon c} = 0.056 \text{ (where } \varepsilon = \text{permittivity)},$$

and fixed relative permittivity $\varepsilon_r$=50. The results show variation in strength of characteristic reflected inductance $$\hat{L}_r \equiv \frac{L_r}{2\pi a N^2}$$

for varying $$\hat{\omega} = \frac{\omega}{\omega_{ref}}.$$

It can be seen from the graph of FIG. 10 that there is a strong dependency in this simple homogeneous model of $\hat{L}_r$ upon $\hat{\omega}$. This was moreover found to be the strongest dependency of $\hat{L}_r$ upon any of the parameters $\hat{h}$, a, $\hat{\sigma}$ or $\varepsilon_r$.

This strong dependency was found to be replicated also in more complex models.

Figure 11:
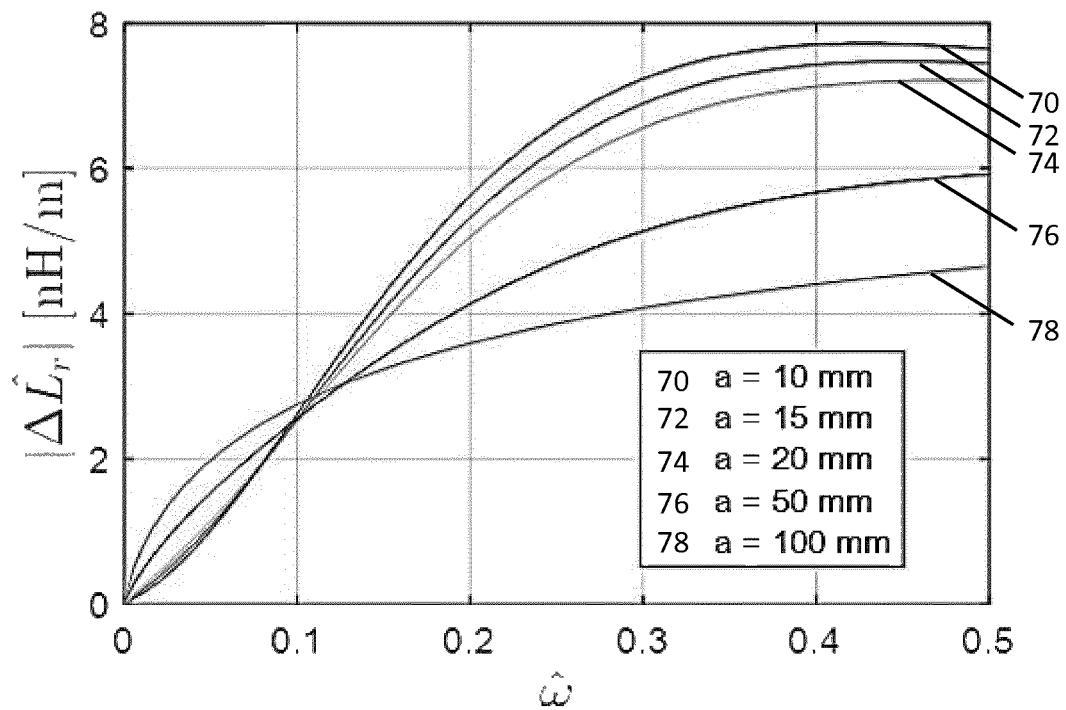

FIG. 11 shows results of computational modelling for $\hat{L}_r$ as a function of $\hat{\omega}$ for a model constructed to represent a bare lung, by which is meant a lung by itself, in isolation of any layers of fat, muscle or bone which in practice surround it. For this model, the change in characteristic reflected inductance $\Delta\hat{L}_r$ between the lung when inflated and the lung when deflated $\Delta\hat{L}_r = L_r$ (inflated)–$L_r$ (deflated) was modelled as a function of $\hat{\omega}$. This change in $\hat{L}_r$ is a significant physiological parameter since it allows determination of characteristics of lung function.

Variation of $\Delta\hat{L}_r$ as a function of $\hat{\omega}$ was modelled for a single-turn loop antenna of five different radii a, ranging from 10 mm to 100 mm. Individual lines 70-78 are shown on the graph corresponding to the different radius sizes, with the radius size for each line indicated by the key in the graph.

It can be seen that there is a strong dependency of $\Delta\hat{L}_r$ upon $\hat{\omega}$ and, again, $\hat{\omega}$ was found to be the parameter upon which $\Delta\hat{L}_r$ was most strongly dependent.

Processing of the electromagnetic signals received from the body in response to the excitation signals may be performed in a number of ways.

In accordance with a first set of embodiments, the signal processing means may be implemented by a phased locked loop. An example of a phased locked loop circuit which may be used in accordance with this set of embodiments is shown in FIG. 12.

In this embodiment, a phase locked loop (PLL) is used to drive a resonator (comprising an antenna 10 and capacitor), and a control signal for the PLL provides an output signal representing the movement of air, fluid and/or tissue in the body of the subject. Hence, the circuit of FIG. 12 implements the functionality of both the signal generation means 62 and the signal processing means 64 of the example system of FIG. 9.

Figure 12:
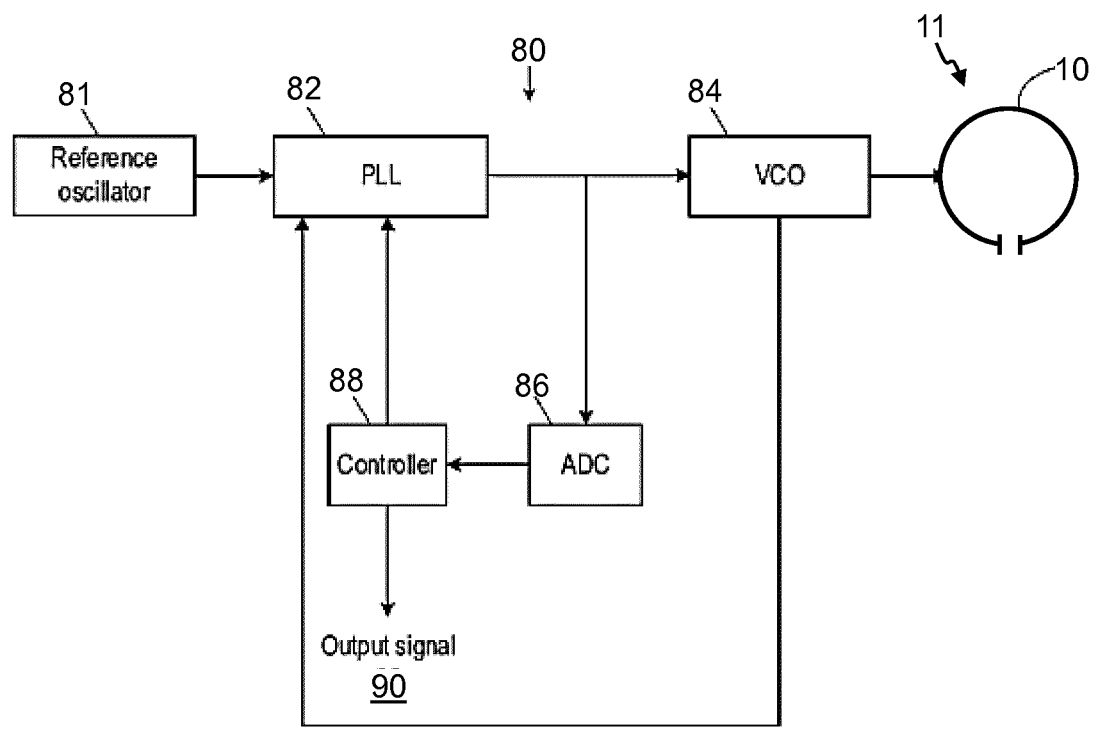
FIG. 12 shows an example sensing device processing circuit in accordance with an embodiment.

FIG. 12 shows signal generation and processing circuitry 80 for the resonator 11, and comprises a reference oscillator 81, a PLL 82 that is connected to the reference oscillator 81 and that outputs an analog control signal (known as Vtune) to a voltage-controlled oscillator (VCO) 84. The Vtune signal is a result of a comparison of the signal from the reference oscillator 81 to the signal from the VCO 84. In response to the PLL analog control signal the VCO 84 generates an excitation signal at a required frequency and provides this to the resonator 11 so that the antenna 10 of the resonator 11 emits the electromagnetic excitation signal(s). As noted above the electromagnetic excitation signal will induce eddy currents in the body of the subject, and these eddy currents will induce a magnetic flux which is sensed by the antenna 10. This generated flux results in a reflected inductance component Lr in the inductance of the antenna coil (as explained above). This can be sensed via detuning of characteristics of the coil, in particular the damping and natural frequency of the coil.

The excitation signal is also provided to the PLL 82 as part of a feedback loop. The analog control signal from the PLL 82 is also provided to an analog-to-digital convertor (ADC) 86 which converts the analog control signal into a digital signal, and this digital signal is provided to a controller 88. The controller 88 determines a digital control signal for the PLL 82 and provides this to the PLL 82. As the skilled person will be aware, in a PLL system, if the phase of the VCO 84 differs from the phase of the reference oscillator 81, the digital control signal corrects the VCO phase.

Movements of air, fluid and/or tissue in the body effectively detune the characteristics of antenna 10 (because of the reflected inductance), and the digital control signal counters this detuning and corrects the phase of the VCO 84. The digital control signal therefore carries information regarding the movements of the air, fluid and/or tissue, and the controller 88 determines an output signal 90 from the digital control signal that represents or contains the information on the movements of air, fluid or tissue in the body of the subject. Although this output signal 90 does not carry the actual phase and amplitude information, the physiological characteristics (e.g. heart rate, breathing rate) are clearly observable.

The correction signal Vtune that is required to keep the VCO 84 at the required frequency is used to measure amplitude and/or phase shifts due to movements of air, fluid and/or tissue in the body of the subject. The phase shifts tend to dominate the amplitude changes. The PLL correction signal (the digital control signal output by the controller 88 derived from the analog PLL correction signal) is used to determine the output signal 90. For example the output signal 90 can correspond to the digital control signal with suitable filtering and/or down-sampling to improve the signal-to-noise ratio.

The output signal hence carries a signal representative of the received electromagnetic signals, derived based on changes in the natural resonance frequency of the resonator 11 which are reflected in the correction signal.

In accordance with a further set of embodiments, an alternative signal processing means is implemented in which sensed signals from the antenna 10 are first processed to reduce their frequency by mixing them with a further reference oscillatory signal of a different frequency and applying a filter which passes the differential frequency. This allows the subsequent signal processing to be performed in a much lower frequency range, which reduces energy consumption and required processing power.

In particular, to reduce energy consumption and required computing power of the system, the signal processing is preferably performed in the digital domain. Digital dividers and counters draw current proportional with the operating frequency. Hence, to further save power it helps to lower the frequencies in the digital system by using a second reference oscillator frequency close to the frequency at which the antenna 10 is driven for generating the electromagnetic excitation signals, and at which the signals returning from the body are also oscillating. By mixing the returned high-frequency electromagnetic signals (typically at around 400-500 MHz) with another signal having a frequency different but close to that frequency (for instance at +/−50 MHz of the EM measurement frequency), and applying a low pass filter which passes the differential frequency (i.e., $f_{measurement}-f_{reference}$), the signal processing (e.g., digital counter) can be performed in a much lower frequency range, which reduces the energy consumption and required processing power.

Figure 13:
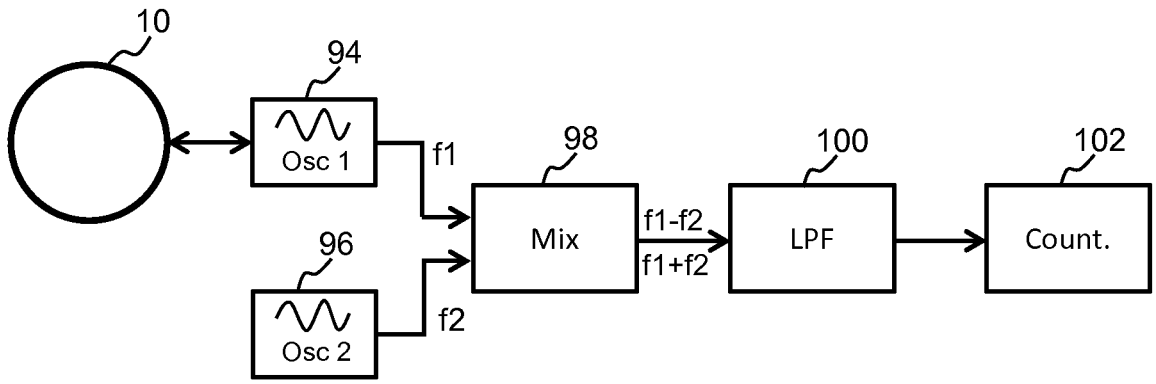
FIG. 13 shows a further example sensing device processing circuit in accordance with an embodiment.

One example of this processing scheme is illustrated in FIG. 13 which shows associated processing circuitry.

The system comprises an antenna 10 coupled to a first oscillator ('Osc 1') 94 which generates an excitation signal for driving the antenna 10 to generate electromagnetic excitation signals for propagation into a body of interest (e.g. a body of a subject). Electromagnetic signals emitted back from the body in response are received at the antenna 10 by inductive coupling and the resultant signal is output from the antenna having frequency f1. A second (reference) oscillator ('Osc 2') 96 generates an oscillatory signal of a second frequency f2 being close to that of f1, for instance between f2=0.8*f1 and f2=1.2*f1 (i.e. within +/−10%-20% of f1).

A mixer ('Mix') 98 mixes the two frequencies f1 and f2, and a low-pass filter ('LPF') 100 then passes the differential frequency (i.e. f1−f2).

The resulting differential frequency signal is then passed to further processing components for deriving properties of the signal received from the body, e.g. in the example of FIG. 13, a counter 102.

In the example of FIG. 13, the first oscillator 94 performs the function of the signal generation means 62 of the system 30 (see FIG. 9) and the remaining shown components perform the function of the signal processing means 64 of the system.

In accordance with one or more examples, the system may comprise a second measurement antenna, this having an associated oscillator for driving the antenna, and wherein this second oscillator is used as the reference oscillator in the processing circuit. Use of two measurement antennas may allow for instance probing of two different parts of the body, for instance two parts of the lung. This may allow differential measurements of the two parts or regions, achieving greater sensitivity to abnormalities. Use of two antennas also enables suppression of movement artefacts and amplification of the measurement signal.

Figure 14:
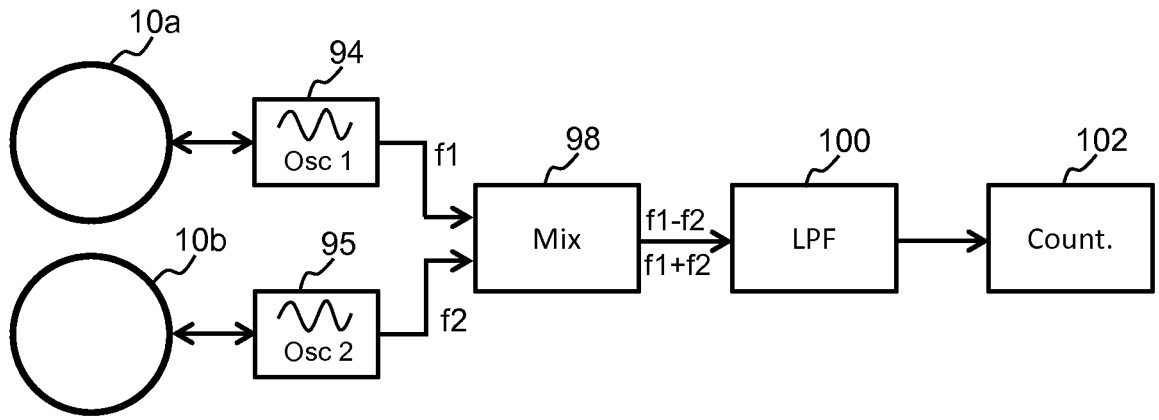
FIG. 14 shows a further example sensing device processing circuit in accordance with an embodiment.

An example is shown in FIG. 14.

A first antenna 10a and second antenna 10b are each connected with an associated oscillator (oscillator 94, and oscillator 95 respectively) for driving the antennas at different respective frequencies f1 and f2, but where these frequencies are close to one another, e.g. between +/−10% to 20% of one another. Electromagnetic signals received back at each of the antenna in response to generated electromagnetic excitation signals will also be at the respective frequencies f1 and f2, and these are mixed with one another by a mixer 98 and a low pass filter 100 applied, configured to pass the differential frequency. This signal is then transferred to further signal processing elements, for instance a counter 102.

Figure 15:
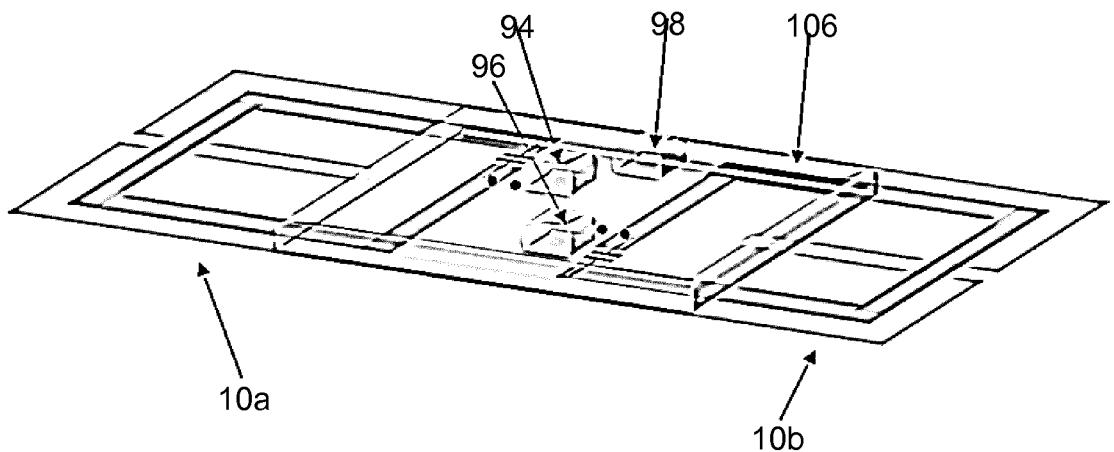
FIG. 15 depicts one example implementation of the example processing circuit of FIG. 14.

One particular implementation of the dual antenna embodiment is schematically illustrated in FIG. 15. The arrangement comprises two antennas 10a, 10b at different ends of an underlying PCB. Each antenna is connected to a respective oscillator (oscillator 94 and 96 respectively). A mixer 98 is provided which mixes the two signals. The filter and further processing elements (e.g. counter) are not shown. The two antennas are part of the same PCB structure and function simultaneously as a component carrier.

The arrangement is covered by an over-all shield 106 which provides protection. The shield however is optional.

This design generates predominantly a magnetic field. In a system with two oscillators such as this, both oscillators couple to each other (i.e., oscillator pulling). The minimum frequency difference (f1−f2) which was obtained in experiments was 11 MHz. In the arrangement illustrated in FIG. 15, the difference implemented was 28 MHz.

The mixer 98 (e.g., a dual-gate MOSFET) mixes a measurement signal carrier with a lower (or higher) frequency, before applying a filter as explained above, to save current and thus power. The resulting frequency signal is then used to derive information, e.g. physiological information, such as e.g. vital signs.

Alternative antenna designs such as loop and gap/slit configurations may alternatively be used in further examples.

The coils and electronics may advantageously all be made in PCB material. However, other suitable materials as may be apparent to the skilled person may also be used.

In all examples of this processing approach, the result is that the RF measurement frequency of typically >200 MHz is reduced to a frequency of ~50 MHz, i.e. the difference between the two mixed frequencies f1, f2. Signals of such a frequency can be easily handled by microcontrollers and microprocessors. Such signals may for instance be directly handled by a microcontroller counter input.

In this way, the use of relatively higher energy-consuming elements such as RF phase-locked loop (PLL) systems and digital frequency dividers is avoided. The system accordingly requires significantly less current.

Alternatively, the use of the mixer and filter arrangement with a lower-frequency phase-locked loop (PLL) could be implemented to improve the quality of the system, although at the expense of greater power consumption.

A further advantage of the present set of embodiments is that mixing does not result in a loss of resolution. By contrast, use of a digital divider does result in such a loss. The sensed signal modulations at the down-mixed 28 MHz signal (taking the example of FIG. 15 presented above) are of the same amplitude (at same relative gain) as the modulations at the higher (e.g. 405 MHz) frequency.

The physiologically modulated 28-MHz signal is then output to low current processing elements, e.g. a counter-input of a frequency-counter of a microcontroller.

Microcontrollers are widely available having counter-inputs able to count frequency shifts in the range which typically occur in the body.

The use of frequency mixing and filtering, in combination with a digital counter, enables measurement of for instance physiological parameters such as vital signs including heartbeat and breathing with a low cost system. The antennas, oscillators, and mixer may in examples all be embedded in a PCB. Flexible circuit technology (such as flex-rigid technology) may also be used to further reduce the size and cost of components and of the overall system.

A test system has been built (which could be further optimized) which draws a 1 mA current per antenna, which is at least 10 times less current than similarly-performing digital systems.

All frequencies presented above are merely exemplary.

Figure 16:
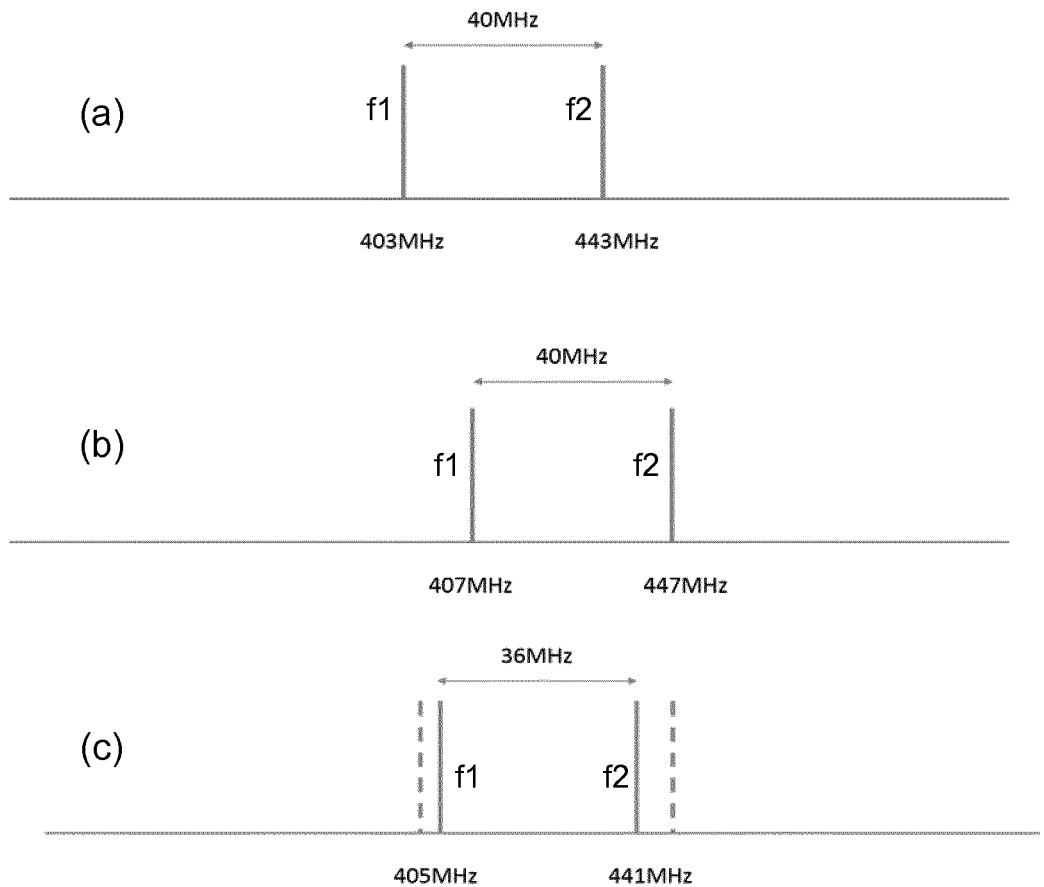
FIG. 16 shows measured signal frequency shifts achieved in use of one embodiment of a sensing device.

FIG. 16 shows the measured shift in frequencies due to probing of the body in the case of the dual antenna embodiment of FIG. 14 or 15. Graph (a) shows the two nominal frequencies f1 and f2 when the antenna is away from any body or medium.

Graph (b) shows the shift in the frequencies as the antenna is brought into proximity with a subject's skin. Both frequencies increase by the same equal amount of 5 Hz.

Graph (c) shows the shift in frequencies during excitation of the body, during which reflected inductance contribution is present. Here, the frequencies shift by different amounts due to the different modulating effects of the different body regions being probed by the two antenna.

Figure 17:
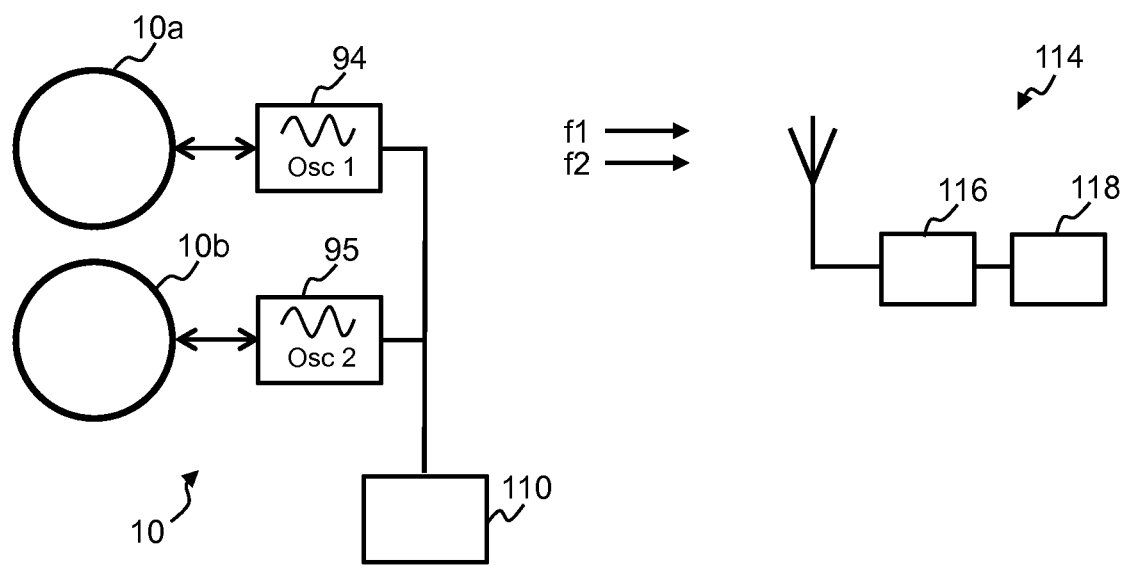
FIG. 17 shows a further example sensing device circuit in accordance with an embodiment, the device making use of a remote processing part.

A further embodiment of the above mixing and filtering processing approach is shown in FIG. 17. In accordance with this embodiment, the mixing and filtering steps are performed remotely. The sensing system 30 itself only performs data collection. The collected signal data is communicated to a remote computer or controller or processor 114. The system comprises only the two antenna 10*a*, 10*b* and the two associated oscillators 94, 65, along with a data communication element 110 for communicating the collected signal data to the remote computer 114 and a battery or other remote power source (not shown).

The remote computer 114 comprises a data communication unit 116 for receiving the signal data from the sensing system 30 and a processing unit 118 which comprises the mixer and filter for deriving the differential frequency signal for communicating to a further processing unit for processing the data.

This embodiment maintains the advantages of reduced power consumption, while minimizing the local hardware requirements. The local sensing probe part of the system can be made with a smaller form factor and with even lower power consumption.

Data communication between the local sensing system 30 and the remote processing part 114 may advantageously be implemented by a wireless communication channel, for instance Wi-Fi, RF communication, ZigBee, NFC or any other wireless protocol or channel. Wireless communication distances of several meters are easily achievable which makes the system highly practical for most applications.

The local sensing system part 30 may in accordance with one or more examples be integrated in a sticking plaster for convenient application to the body. This is achievable due to the very small form factor realizable in this remote processing example.

The remote processing part 114 may be implemented in a Software Defined Radio (SDR) system in accordance with one or more examples.

A system for creating or inductively measuring a magnetic field is often theoretically modelled as an infinitely small sized loop for generating or receiving magnetic fields, with infinitely small sized connection wires. In real world applications however, when attempting to measure small signals from the human body in the near-field, the behavior of the parasitic effects in all components of the measurement system can dominate the measurement. Suppressing such effects is therefore important for improving signal to noise ratio. Embodiments of the present invention have provided various means for facilitating such field suppression.

The shielded antenna devices of the invention are susceptible to various applications.

In general, the system may be used to probe internal properties of any body or object in which there is capacity for eddy currents to form in response to application of oscillating magnetic fields. The system may be particularly useful for probing systems with dynamic interiors, i.e. interiors in which composing parts or portions move or change in size, since such changes and movements cause detectable modulations in sensed signals, allowing for measurement and other analysis.

One particularly advantageous area of application is that of probing the human or animal body. The system allows for measurement or other analysis of movement of air of fluid (e.g. blood) within the body or of the expansion or contraction of organs or vessels such as the heart, the lungs or blood vessels for example.

Any embodiment of the invention may be advantageously applied to measuring vital signs in accordance with one set of examples. This includes for instance heart rate, pulse rate, breathing capacity and breathing rate.

The technology may in examples be advantageously embedded in small, wearable structures used for vital sign monitoring. The technology could also be used for wearable fetal monitoring and unobtrusive neonatal monitoring.

The structure may be made in rigid or flexible PCB material thin enough to be embodied in a magnetic sensor (sticking) plaster.

In accordance with any embodiment, the device may be used for sensing physiological parameters and properties, for instance air, fluid and/or tissue movements in the body of a subject, e.g. the human body. The system may be advantageously applied in particular for sensing breathing movements for instance.

In these examples, the system senses air, fluid and/or tissue movements (e.g. caused by breathing or the beating of the heart) by sensing modulations in the reflected inductance of the signal caused by these movements.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An inductive sensing device for sensing electromagnetic signals emitted from a medium in response to propagation into the medium of electromagnetic excitation signals, the inductive sensing device comprising:
   a loop antenna for inductively coupling with said electromagnetic signals emitted from the medium; and
   a blocking shield arranged to intercept electromagnetic signals propagating to or from the antenna, the blocking shield including an electrically conductive body for blocking electrical components of incident signals, and wherein the electrically conductive body delimits at least one non-conductive gap for inhibiting induction of eddy currents within the electrically conductive body, wherein the loop antenna is broken by an opening, the opening being bridged by a capacitor, such that the capacitor divides the loop antenna into two wing parts, the wing parts extending to either side of the capacitor; and
   a signal processing means, the means being electrically coupled to the antenna via only a single point of the antenna, located to one side of the opening.

2. The inductive sensing device as claimed in claim 1, wherein the device is a physiological inductive sensing device for sensing one or more physiological characteristics of a body of a subject.

3. The inductive sensing device as claimed in claim 1, wherein the blocking shield is arranged facing the antenna loop, and with the at least one gap aligned such as to extend across a circumference of the loop antenna.

4. The inductive sensing device as claimed in claim 1, wherein the blocking shield includes a plate element, arranged facing one planar side of the loop antenna.

5. The inductive sensing device as claimed in claim 1, wherein one of:
   the blocking shield includes a grounded plate element and the loop antenna is electrically coupled to the plate element in order to ground the loop; or
   the loop antenna is coupled to the blocking shield via a capacitor.

6. The inductive sensing device as claimed in claim 5, wherein the loop antenna is electrically coupled to the plate element via an outer conductor of a coaxial cable, and
   wherein an inner conductor of the co-axial cable is further coupled to the antenna for providing connection between the antenna and the signal processing means.

7. The inductive sensing device as claimed in claim 1, wherein one of:
   the at least one gap extends inwardly from an edge of the electrically conductive body or
   the gap extends from said edge to at least a central point of the electrically conductive body.

8. The inductive sensing device as claimed in claim 1, wherein the at least one gap is one of:
   an opening through the electrically conductive body; a slot in the electrically conductive body; or
   a slit in the electrically conductive body.

9. The inductive sensing device as claimed in claim 1, wherein the blocking shield extends coaxially around a perimeter of the loop antenna.

10. The inductive sensing device as claimed in claim 1, further comprising,
    a secondary shielding element adapted to block electromagnetic signals, the shielding element arranged to shield one or both of the capacitor bridging the loop antenna and the connection point between the loop antenna and the signal processing means, and
    wherein the secondary shielding element is a shielding enclosure arranged to enclose one or both of the capacitor bridging the loop antenna and the connection point between the loop antenna and the signal processing means.

11. The inductive sensing device as claimed in claim 1, wherein the loop antenna and bridging capacitor form a resonator for generating the electromagnetic excitation signals for propagation into the medium, and
    wherein the device further comprises a signal generation means adapted in use to excite the loop antenna to generate the excitation signals.

12. The inductive sensing device as claimed in claim 11, wherein the device is adapted to generate electromagnetic excitation signals with a radial frequency co for propagating into said medium,
    wherein a normalized radial frequency $$\hat{\omega} \equiv \frac{\omega}{\omega_{ref}}$$

of the electromagnetic excitation signals is from 0.025 to 0.50, where $\omega_{ref}$2πc/l and c=the speed of light and l is a circumferential length of a single winding of the loop antenna.

13. The inductive sensing device as claimed in claim 1, wherein the signal processing means is adapted to process signals received at the loop antenna and to downscale a frequency of the signals by mixing each signal with a reference oscillatory signal of a different frequency, and is further adapted to apply a differential filter to derive an output signal having a frequency being the difference between the frequency of the oscillatory signal and the received signal.

14. The inductive sensing device as claimed in claim 13, wherein the frequency of the reference oscillatory signal and the frequency of the received signals is from 10 to 20% apart.

15. An inductive sensing method for sensing electromagnetic signals emitted from a medium in response to propagation into the medium of electromagnetic excitation signals, the inductive sensing method comprising:
    using a loop antenna to inductively couple with the electromagnetic signals emitted from the medium in order to sense said signals, wherein a blocking shield is arranged in a propagation path of the loop antenna for intercepting electromagnetic signals propagating to or from the loop antenna, the blocking shield including an electrically conductive body for blocking electrical components of incident signals, and wherein the electrically conductive body delimits at least one non-conductive gap for inhibiting induction of eddy currents within the electrically conductive body, and wherein the loop antenna is broken by an opening, the opening being bridged by a capacitor, such that the capacitor divides the loop antenna into two wing parts, the wing parts extending to either side of the capacitor, and wherein a signal processing means is electrically coupled to the antenna via only a single point of the antenna, located to one side of the opening.

\* \* \* \* \*